United States Patent [19]
Mao et al.

[11] Patent Number: 6,130,101
[45] Date of Patent: Oct. 10, 2000

[54] SULFONATED XANTHENE DERIVATIVES

[75] Inventors: Fei Mao; Wai-Yee Leung; Richard P. Haugland, all of Eugene, Oreg.

[73] Assignee: Molecular Probes, Inc., Eugene, Oreg.

[21] Appl. No.: 08/935,963

[22] Filed: Sep. 23, 1997

[51] Int. Cl.[7] .................. G01N 33/533; G01N 33/554; C07K 16/12; C07K 16/18; C07D 311/82

[52] U.S. Cl. .................. 436/546; 435/6; 435/7.21; 435/7.37; 436/529; 436/531; 436/800; 436/837; 436/829; 530/391.3; 530/391.5; 530/402; 544/70; 544/79; 544/129; 544/130; 544/141; 544/231; 544/260; 544/364; 544/372; 544/375; 546/18; 546/37; 546/41; 546/48; 546/62; 546/187; 548/407; 548/418; 548/426; 548/525; 549/14; 549/33; 549/40; 549/223; 549/225; 549/226; 549/227

[58] Field of Search ...................... ; G01N 33/533, G01N 33/554; C07K 16/12, 16/18

[56] References Cited

U.S. PATENT DOCUMENTS

| | | | |
|---|---|---|---|
| 4,439,356 | 3/1984 | Khanna et al. | 435/7 |
| 4,473,693 | 9/1984 | Stewart | 546/100 |
| 4,557,862 | 12/1985 | Mangel et al. | 436/800 |
| 4,711,955 | 12/1987 | Ward et al. | 536/29 |
| 4,900,686 | 2/1990 | Arnost et al. | 436/546 |
| 4,997,928 | 3/1991 | Hobbs, Jr. | 536/27 |
| 5,047,519 | 9/1991 | Hobbs, Jr. et al. | 544/243 |
| 5,049,673 | 9/1991 | Tsien et al. | 546/107 |
| 5,137,810 | 8/1992 | Sizemore et al. | 435/7.32 |
| 5,171,534 | 12/1992 | Smith et al. | 436/94 |
| 5,196,306 | 3/1993 | Bobrow et al. | 435/7.9 |
| 5,208,148 | 5/1993 | Haugland et al. | 435/14 |
| 5,227,487 | 7/1993 | Haugland et al. | 546/15 |
| 5,268,486 | 12/1993 | Waggoner et al. | 548/427 |
| 5,332,666 | 7/1994 | Prober et al. | 435/6 |
| 5,405,975 | 4/1995 | Kuhn et al. | 549/347 |
| 5,451,343 | 9/1995 | Neckers et al. | 252/582 |
| 5,453,517 | 9/1995 | Kuhn et al. | 549/227 |
| 5,514,710 | 5/1996 | Haugland et al. | 514/512 |
| 5,516,911 | 5/1996 | London et al. | 548/236 |
| 5,635,608 | 6/1997 | Haugland et al. | 536/1.11 |
| 5,648,270 | 7/1997 | Kuhn et al. | 436/74 |
| 5,696,157 | 12/1997 | Wang et al. | 514/457 |
| 5,750,409 | 5/1998 | Herrmann et al. | 436/517 |
| 5,792,389 | 8/1998 | Hammond et al. | 252/582 |

FOREIGN PATENT DOCUMENTS

| | | |
|---|---|---|
| 515133 | 11/1992 | European Pat. Off. |
| 4137934 A1 | of 1993 | Germany . |
| 58-187473 | 11/1983 | Japan . |
| W 94/05688 | of 1994 | WIPO . |

OTHER PUBLICATIONS

Raju et al., Am. J. Physiol. 256, C540 (1989).
R. Haugland, Molecular Probes Handbook of Fluorescent Probes and Research Chemicals; Chapter 1–3 (1996).
Brinkley, Bioconjugate Chem., 3, 2 (1992).
Gee et al. Tet. Lett, 37, 7905 (1996).
McKinney et al. J. Org. Chem. 27, 3986 (1962).
Amlaiky et al., Febs Lett 176, 436 (1984).
Haugland et al., Meth. Mol. Biol. 45, 205 (1995).
Haugland et al., Meth. Mol. Biol. 45, 223 (1995).
Haugland et al. Meth. Mol. Biol. 45, 235 (1995).
Kendall et al., J. Biol. Chem. 257, 13892 (1982).
Szoka, Jr. et al., Proc. Natl. Acad. Sci. USA 75, 4194 (1978).
Szoka, Jr. et al. Ann Rev. Biophys. Bioeng. 9, 467 (1980).
Blankenfeld et al. J. Neurosci. Meth. 36, 309 (1991).
Chem Abst. 101:40006s (1983).
Chemical Abstract 65:9998d, 1996.
N. Abrosimova et al, Chemical Abstract 108:223089, 1982.
J. Bae et al, Chemical Abstract 97:181834, 1982.

*Primary Examiner*—Mary E. Ceperley
*Attorney, Agent, or Firm*—Anton E. Skaugset

[57] ABSTRACT

The present invention describes xanthene dyes, including rhodamines, rhodols and fluoresceins that are substituted one or more times by a sulfonic acid or a salt of a sulfonic acid. The dyes of the invention, including chemically reactive dyes and dye-conjugates are useful as fluorescent probes, particularly in biological samples.

73 Claims, 6 Drawing Sheets

SULFONATED XANTHENE DERIVATIVES

FIELD OF THE INVENTION

The invention relates to novel sulfonated xanthene dyes (including rhodamines, fluoresceins and rhodol dyes), reactive dye derivatives, and dye-conjugates; and to their use in biological systems.

BACKGROUND OF THE INVENTION

Fluorescent dyes are known to be particularly suitable for biological applications in which a highly sensitive detection reagent is desirable. Fluorescent dyes are used to impart both visible color and fluorescence to other materials. The dyes of this invention are sulfonated derivatives of xanthene-based dyes that are typically fluorescein, rhodol or rhodamine derivatives.

"Fluorescein" dyes include derivatives of 3H-xanthen-6-ol-3-one that are typically substituted at the 9-position by a 2-carboxyphenyl group. "Rhodol" dyes include derivatives of 6-amino-3H-xanthen-3-one that are typically substituted at the 9-position by a 2-carboxyphenyl group. "Rhodamine" dyes include derivatives of 6-amino-3H-xanthen-3-imine that are typically substituted at the 9-position by a 2-carboxyphenyl group.

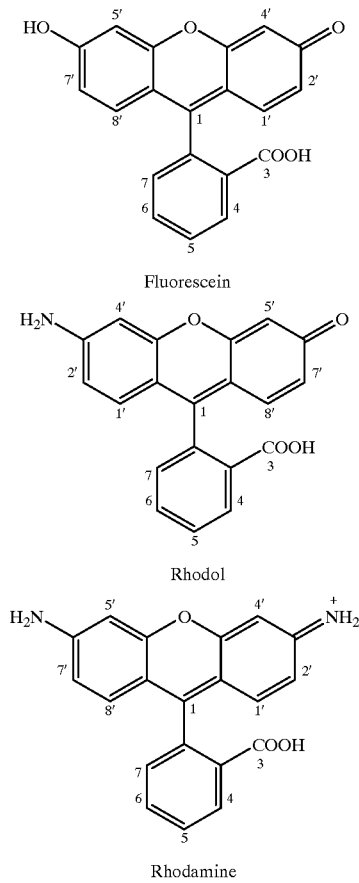

Fluorescein

Rhodol

Rhodamine

Rhodols, rhodamines and fluoresceins are typically substituted by a derivative capable of forming a 5- or 6-membered lactone or lactam ring. For example in the case of fluorescein the spirolactone form of the dye has the structure:

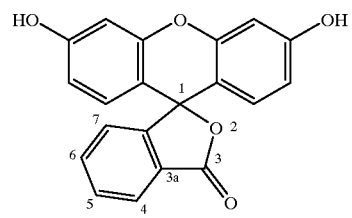

Sulfonation of some cyanine dyes has been shown to decrease the inherent tendency of those dyes to form dimers and aggregates, presumably due to the increased polar character imparted by the sulfonic acid moiety (Waggoner et al. U.S. Pat. No. 5,268,486 (1993)). Ring sulfonation increases the brightness of some fluorescent dyes, including carbocyanine dyes (co-pending application Ser. No. 08/702,396 by Leung et al., filed Aug. 14, 1996) and coumarin dyes (co-pending application Ser. No. 08/749,753 by Wang et al., filed Nov. 15, 1996, now allowed).

The present invention describes xanthene dyes, including fluorescein, rhodol and rhodamine dyes, that are substituted by at least one sulfonate moiety. The sulfonated xanthene dyes of the invention possess considerable advantages over their non-sulfonated analogs. In particular, their fluorescence yields are typically higher than those of other dyes having comparable spectra, including fluorescein, CY-2, tetramethylrhodamine, CY-3 and TEXAS RED dye (Table 5). The sulfonated dyes of the invention exhibit resistance to quenching upon protein conjugation (FIG. 3). In addition, the dyes of the invention possess better photostability than fluorescein or the sulfonated cyanine CY2 and CY3 dyes (as shown in FIG. 6). The spectra of the sulfonated rhodamine dyes of the invention are insensitive to pH changes in the range between pH 4 and 10. Also, the dyes of the invention possess substantially greater water solubility than non-sulfonated analogs.

SUMMARY OF THE INVENTION AND DESCRIPTION OF PREFERRED EMBODIMENTS

Figure 1:
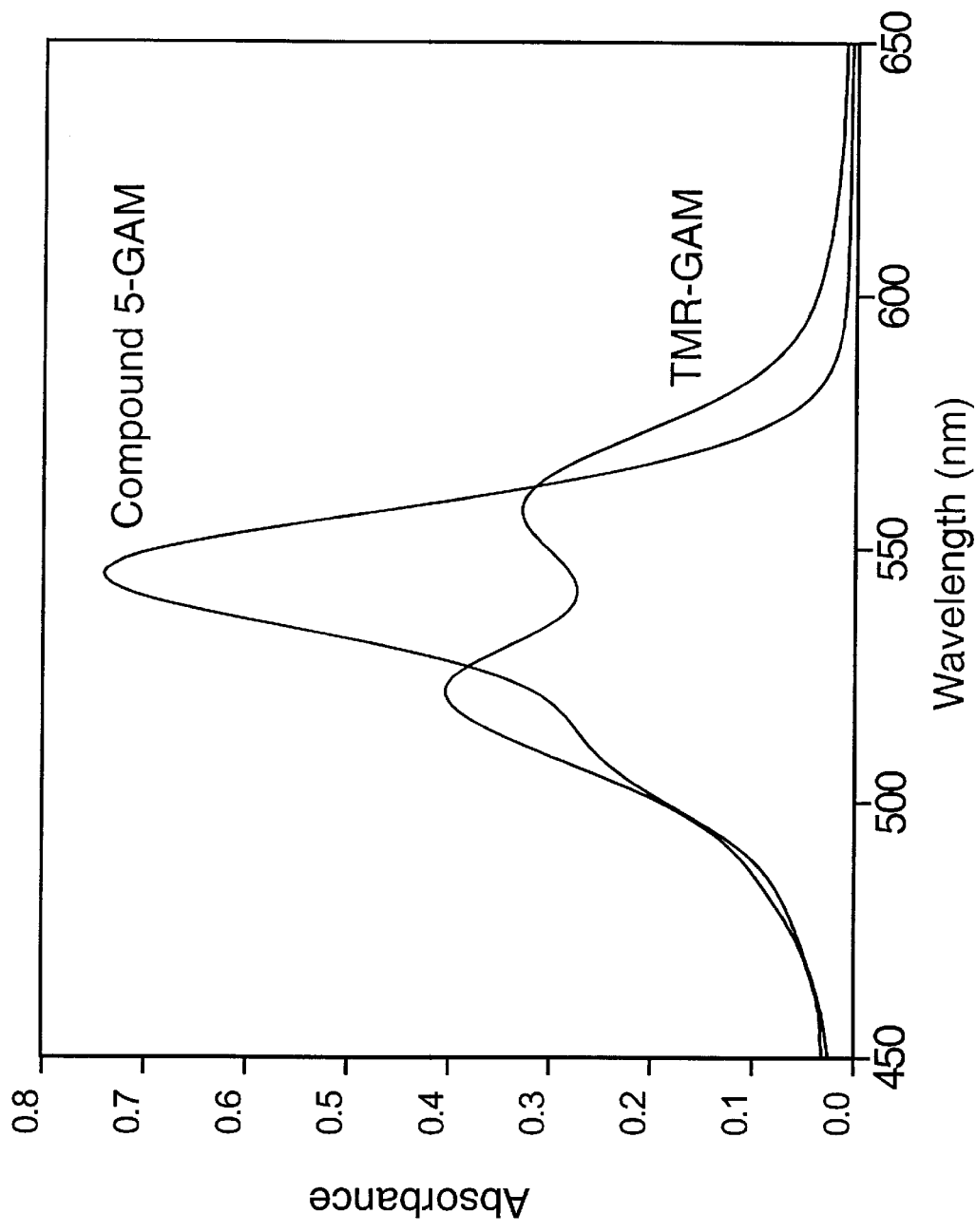
FIG. 1: The absorption spectra of goat anti-mouse (GAM) IgG conjugates of Compound 5 (Compound 5-GAM) and tetramethylrhodamine (TMR-GAM), as described in Example 38.

The present invention describes xanthene dyes that are substituted one or more times by a sulfonic acid or a salt of a sulfonic acid that are useful as fluorescent probes. The dyes of the invention optionally possess a reactive group useful for preparing fluorescent conjugates, which conjugates and methods for their preparation and use are described herein.

The compounds of the invention are xanthenes, including fluoresceins, rhodamines and rhodols, that are substituted one or more times by —$SO_3X$ or —$CH_2SO_3X$, where X is H (sulfonic acid), or a counterion (salt of a sulfonic acid). As used herein, where X is a counterion, it is typically a cation that is not toxic as used, and does not have a substantially deleterious effect on biomolecules. Examples of suitable cations include, among others, $K^+$, $Na^+$, $Cs^+$, $Li^+$, $Ca^{2+}$, $Mg^{2+}$, ammonium, alkylammonium or alkoxyammonium salts, or pyridinium salts. Alternatively, the counterion of the sulfonic acid may form an inner salt with a positively charged atom on the xanthene dye itself, typically the quaternary nitrogen atom of a rhodamine dye.

In one embodiment, the dyes have the formula

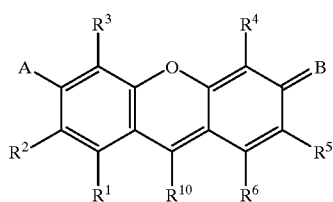

Formula I or the formula

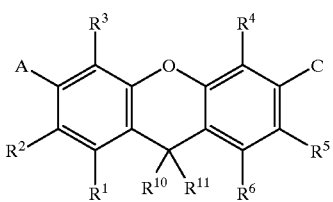

Formula II

Substituents $R^2$, $R^3$, $R^4$ and $R^5$ are independently H, F, Cl, Br, I, CN; or $C_1$–$C_{18}$ alkyl, or $C_1$–$C_{18}$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol. Alternatively one or more of $R^2$, $R^3$, $R^4$ and $R^5$ are —$SO_3X$, or —L-$R_x$, or —L-$S_c$, where L is a covalent linkage, $R_x$ is a reactive group, and $S_c$ is a conjugated substance. In a preferred embodiment, $R^3$ and $R^4$ are each —$SO_3X$.

Substituents $R^1$ and $R^6$ are H, or $R^1$ taken in combination with $R^2$, or $R^5$ taken in combination with $R^6$, or both, form a fused aromatic six membered ring, that is optionally substituted by one or more —$SO_3X$ moieties.

In one embodiment of the invention, $R^2$, $R^3$, $R^4$ and $R^5$ are independently H, F, Cl, Br, I or $C_1$–$C_{18}$ alkyl. In another embodiment of the invention, $R^1$, $R^2$, $R^5$ and $R^6$ are H. In yet another embodiment of the invention, $R^2$ and $R^5$ are each F or Cl.

The A moiety is $OR^7$, where $R^7$ is H, $C_1$–$C_{18}$ alkyl, or —L-$R_x$, or —L-$S_c$. Alternatively, A is $NR^8R^9$ where $R^8$ and $R^9$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, where the alkyl portions each are independently and optionally substituted by amino, hydroxy, carboxylic acid, a salt of carboxylic acid, or a carboxylic acid ester of a $C_1$–$C_6$ alkyl. Alternatively, $R^8$ in combination with $R^9$ forms a saturated 5- or 6-membered heterocycle that is a piperidine, a morpholine, a pyrrolidine or a piperazine, each of which is optionally substituted by methyl, carboxylic acid, a salt of carboxylic acid, or a carboxylic acid ester of a $C_1$–$C_6$ alkyl. In another alternative, one or both of $R^8$ and $R^9$ are —L-$R_x$ or —L-$S_c$.

In another aspect of the invention, $R^8$ in combination with $R^2$, or $R^9$ in combination with $R^3$, or both, form a 5- or 6-membered ring that is saturated or unsaturated, and is optionally substituted by one or more $C_1$–$C_6$ alkyls or —$CH_2SO_3X$ moieties.

The B moiety, when present, is O or $N^+R^{18}R^{19}$, where $R^{18}$ and $R^{19}$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alkyl. Alternatively, $R^{18}$ in combination with $R^{19}$ forms a saturated 5- or 6-membered heterocycle that is a piperidine, a morpholine, a pyrrolidine or a piperazine, each of which is optionally substituted by methyl, carboxylic acid, a salt of carboxylic acid, or a carboxylic acid ester of a $C_1$–$C_6$ alkyl. In another alternative, one or both of $R^{18}$ and $R^{19}$ are —L-$R_x$, or —L-$S_c$.

In another aspect of the invention, $R^{18}$ in combination with $R^4$, or $R^{19}$ in combination with $R^5$, or both, form a 5- or 6-membered ring that is saturated or unsaturated, and is optionally substituted by one or more $C_1$–$C_6$ alkyls or —$CH_2SO_3X$ moieties.

The C moiety, when present, is $OR^{17}$, where $R^{17}$ is H, $C_1$–$C_{18}$ alkyl, or —L-$R_x$, or —L-$S_c$. Alternatively, C is $NR^{18}R^{19}$ where $R^{18}$ and $R^{19}$ are as defined previously.

In one embodiment of the invention, $R^9$ and $R^{18}$ are independently H, or carboxyalkyl, salt of carboxyalkyl, sulfoalkyl or a salt of sulfoalkyl, each having 1–6 carbons. Typically $R^9$ and $R^{18}$ are H, methyl or ethyl.

In another embodiment of the invention, $R^8$ in combination with $R^2$ and $R^{19}$ in combination with $R^5$ independently form 5- or 6-membered rings that are saturated or unsaturated, and are optionally substituted by one or more alkyl groups having 1–6 carbons, or by one or more —$CH_2SO_3X$ moieties. In yet another embodiment of the invention, $R^8$ in combination with $R^2$ and $R^{19}$ in combination with $R^5$ independently form 5- or 6-membered rings that are saturated, and are substituted by one or more —$CH_2SO_3X$ moieties. Some (but not all) examples of fused 5- or 6-membered rings as described herein are provided below (additional substituents, such as sulfonic acid or sulfomethyl moieties not shown).

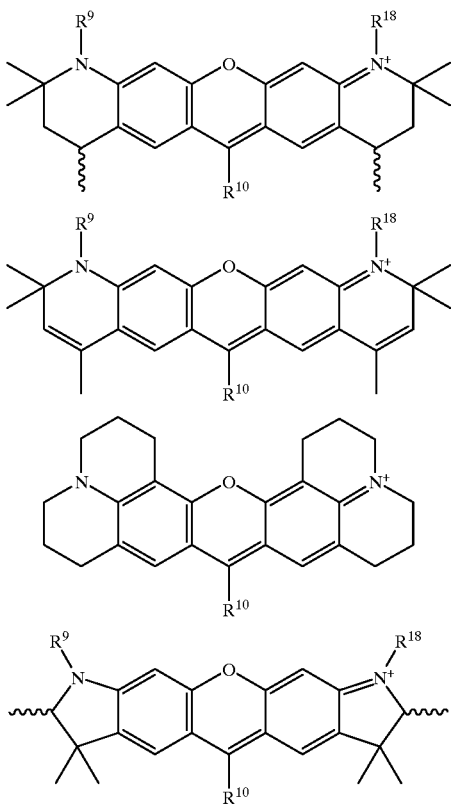

The substituent $R^{10}$ is H, F, CN, a carboxylic acid, a salt of carboxylic acid, or a carboxylic acid ester of a $C_1$–$C_6$ alcohol. Alternatively $R^{10}$ is a saturated or unsaturated $C_1$–$C_{18}$ alkyl that is optionally substituted one or more times by F, Cl, Br, carboxylic acid, a salt of carboxylic acid, a carboxylic acid ester of a $C_1$–$C_6$ alcohol, —$SO_3$X, amino, alkylamino, or dialkylamino, the alkyl groups of each substituent having 1–6 carbons. $R^{10}$ is optionally —L-$R_x$ or —L-$S_c$.

In another embodiment of the invention, $R^{10}$ is an aryl substituent having the formula

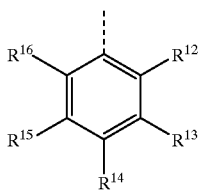

where the $R^{12}$, $R^{13}$, $R^{14}$, $R^{15}$ and $R^{16}$ substituents are independently H, F, Cl, Br, I, —$SO_3$X, a carboxylic acid, a salt of carboxylic acid, CN, nitro, hydroxy, azido, amino, hydrazino, or $R^{12}$, $R^{13}$, $R^{14}$, $R^{15}$ and $R^{16}$ are independently $C_1$–$C_{18}$ alkyl, $C_1$–$C_{18}$ alkoxy, $C_1$–$C_{18}$ alkylthio, $C_1$–$C_{18}$ alkanoylamino, $C_1$–$C_{18}$ alkylaminocarbonyl, $C_2$–$C_{36}$ dialkylaminocarbonyl, $C_1$–$C_{18}$ alkyloxycarbonyl, or $C_6$–$C_{18}$ arylcarboxamido, the alkyl or aryl portions of which are optionally substituted one or more times by F, Cl, Br, I, hydroxy, carboxylic acid, a salt of carboxylic acid, a carboxylic acid ester of a $C_1$–$C_6$ alcohol, —$SO_3$X, amino, alkylamino, dialkylamino or alkoxy, the alkyl portions of these substituents in turn having 1–6 carbons. Alternatively, one pair of adjacent substituents $R^{13}$ and $R^{14}$, $R^{14}$ and $R^{15}$ or $R^{15}$ and $R^{16}$, when taken in combination, form a fused 6-membered aromatic ring that is optionally further substituted by carboxylic acid, or a salt of carboxylic acid. Alternatively, one of $R^{12}$, $R^{13}$, $R^{14}$, $R^{15}$ and $R^{16}$ is —L-$R_x$ or —L-$S_c$.

In one embodiment of the invention, $R^{12}$, $R^{13}$, $R^{14}$, $R^{15}$, and $R^{16}$ are independently H, Cl, F, amino, nitro, —$SO_3$X, a carboxylic acid, a salt of carboxylic acid, or a carboxy-substituted alkylthio having the formula —S-$(CH_2)_n$COOH, where n is 1–15. In another embodiment of the invention, at least three of $R^{13}$, $R^{14}$, $R^{15}$, and $R^{16}$ are F or Cl. In another embodiment of the invention, one of $R^{14}$ and $R^{15}$ is a carboxylic acid, a salt of a carboxylic acid, or —S-$(CH_2)_n$COOH, where n is 1–15, and the other of $R^{14}$ and $R^{15}$ is H, F or Cl.

The $R^{11}$ substituent is H, hydroxy, CN or a $C_1$–$C_6$ alkoxy. In another embodiment of the invention, $R^{10}$ in combination with $R^{11}$ forms a 5-membered spirolactone ring or a 5-membered spirosultone ring. Alternatively, $R^{11}$ in combination with $R^{12}$ forms a 5- or 6-membered spirolactone ring or a 5- or 6-membered spirosultone ring, for example (additional substituents are not shown):

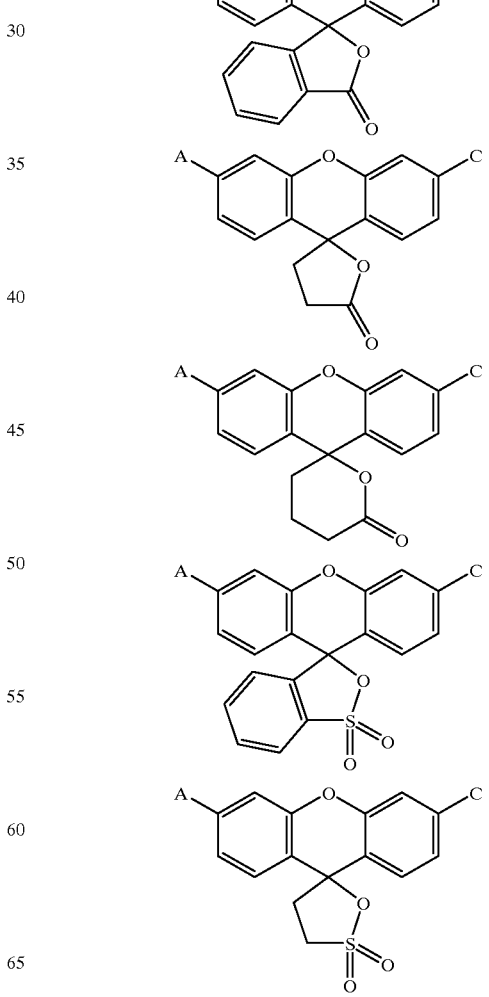

-continued

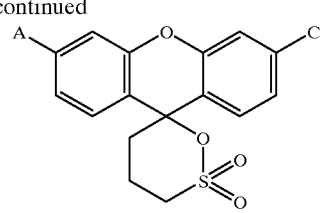

The methylene carbons of the spirolactone ring or spirosultone ring are optionally and independently substituted by H, F or $CH_3$.

Alternatively, $R^{10}$ together with $R^{11}$ is a carbonyl oxygen, according to the simplified formula below (additional substituents are not shown).

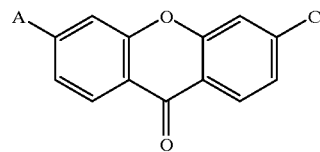

Dye embodiments that incorporate a spirolactone ring are representative of a structural isomer that may exist in equilibrium with the isomer wherein $R^{12}$ is a carboxylic acid, or $R^{10}$ is a propionic or butyric acid. Dyes that incorporate a spirosultone ring may exist in equilibrium with the isomer wherein $R^{12}$ is a sulfonic acid, or $R^{10}$ is a sulfonic acid-substituted ethyl or propyl. Isomers that incorporate a spirolactone or spirosultone ring are non-fluorescent until the ring is opened.

Where A is $OR^7$, B is O, $R^{10}$ is aryl and $R^{12}$ is carboxy or —$SO_3X$, the described dye is a fluorescein (Formula I). Where A is $OR^7$ and C is $OR^{17}$, $R^{10}$ is aryl, $R_{11}$ is H, and $R^{12}$ is carboxy or —$SO_3X$, the described dye is a dihydrofluorescein (Formula II). Where A is $NR^8R^9$, B is O, $R^{10}$ is aryl and $R^{12}$ is carboxy, the described dye is a rhodol (Formula I). Where A is $NR^8R^9$, C is $OR^{17}$, $R^{10}$ is aryl, $R^{11}$ is H, and $R^{12}$ is carboxy, the dye is a dihydrorhodol (Formula II). Where A is $NR^8R^9$, B is $N^+R^{18}R^{19}$, $R^{10}$ is aryl, and $R^{12}$ is carboxy, the described dye is a rhodamine. Where A is $NR^8R^9$, C is $NR^{18}R^{19}$, $R^{10}$ is aryl, $R^{11}$ is H, and $R^{12}$ is carboxy, the described dye is a dihydrorhodamine. Where the dyes of the invention are fluoresceins, they are preferably sulfonefluoresceins (wherein $R^{12}$ is —$SO_3X$). Preferably, the dyes of the invention are rhodamines or rhodols, more preferably rhodamines.

In one embodiment of the invention, at least one of $R^2$, $R^3$, $R^4$, and $R^5$ is —$SO_3X$, preferably $R^3$ and $R^4$ are —$SO_3X$. In another embodiment of the invention, $R^1$ taken in combination with $R^2$, or $R^5$ taken in combination with $R^6$, or both, form a fused aromatic six-membered ring that is substituted by at least one —$SO_3X$ moiety. In another embodiment of the invention $R^8$ in combination with $R^2$, or $R^9$ in combination with $R^3$, or $R^{18}$ in combination with $R^4$, or $R^{19}$ in combination with $R^5$, form a 5- or 6-membered ring that is saturated or unsaturated, and is substituted by at least one —$CH_2SO_3X$ moiety. Preferably $R^8$ in combination with $R^2$ and $R^{19}$ in combination with $R^5$, form a 5- or 6-membered ring that is saturated or unsaturated, and is substituted by at least one —$CH_2SO_3X$ moiety.

Spectral properties of selected dyes are given in Table 1.

TABLE 1

Spectral properties of selected fluorophores of the invention

| Fluorophore | Absorbance maximum (nm) | Emission maximum (nm) |
| --- | --- | --- |
| Compound 1 | 491 | 515 |

TABLE 1-continued
Spectral properties of selected fluorophores of the invention
| Fluorophore | Absorbance maximum (nm) | Emission maximum (nm) |
|---|---|---|
| 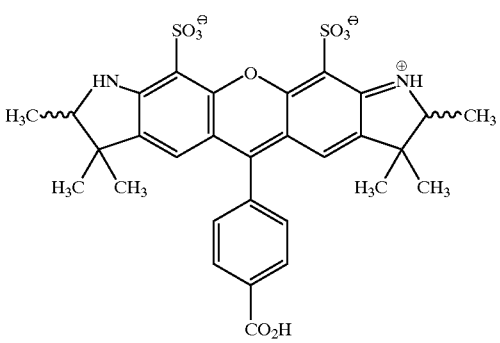<br>Compound 4 | 523 | 548 |
| 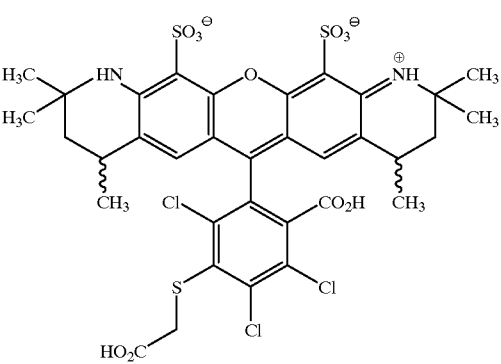<br>Compound 5 | 553 | 569 |
| 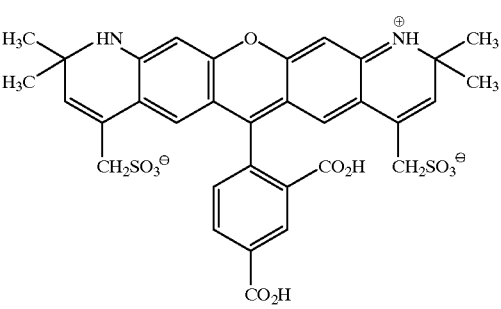<br>Compound 14 | 573 | 596 |
| 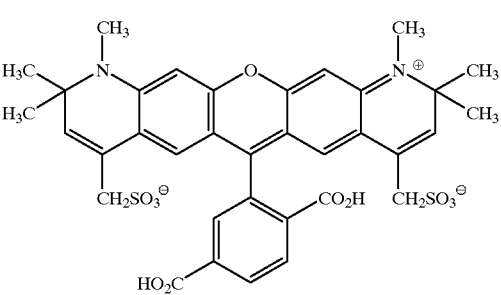<br>Compound 7 | 585 | 610 |

TABLE 1-continued
Spectral properties of selected fluorophores of the invention
| Fluorophore | Absorbance maximum (nm) | Emission maximum (nm) |
|---|---|---|
| 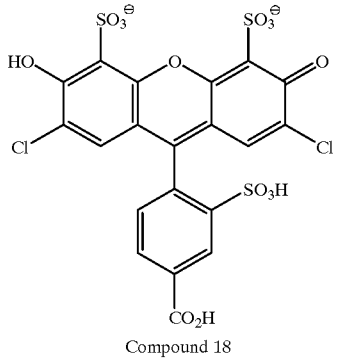 Compound 18 | 506 (pH 9) | 522 (pH 9) |
| 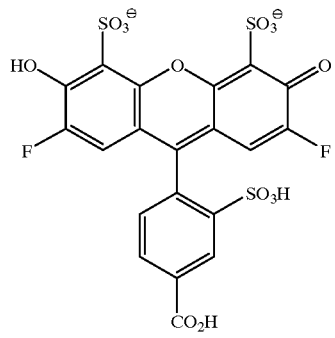 Compound 39 | 496 (pH 9) | 514 (pH 9) |
| 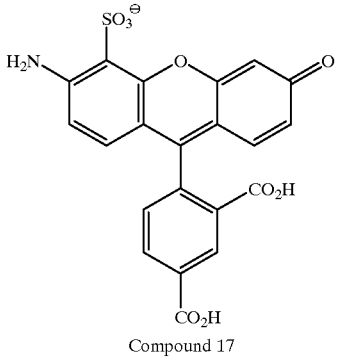 Compound 17 | 493 (pH 9) | 518 (pH 9) |

TABLE 1-continued

Spectral properties of selected fluorophores of the invention

| Fluorophore | Absorbance maximum (nm) | Emission maximum (nm) |
|---|---|---|
| Compound 32 (structure shown) | 615 | 632 |

Conjugates of Reactive Dyes

In one embodiment of the invention, the sulfonated xanthene contains at least one group —L-$R_x$, where $R_x$ is the reactive group that is attached to the fluorophore by a covalent linkage L. In certain embodiments, the covalent linkage attaching the sulfonated xanthene to $R_x$ contains multiple intervening atoms that serve as a spacer. The dyes with a reactive group ($R_x$) fluorescently label a wide variety of organic or inorganic substances that contain or are modified to contain functional groups with suitable reactivity, resulting in chemical attachment of the conjugated substance ($S_c$), represented by —L-$S_c$. The reactive group and functional group are typically an electrophile and a nucleophile that can generate a covalent linkage. Alternatively, the reactive group is a photoactivatable group, and becomes chemically reactive only after illumination with light of an appropriate wavelength. Typically, the conjugation reaction between the reactive dye and the substance to be conjugated results in one or more atoms of the reactive group $R_x$ to be incorporated into a new linkage L attaching the sulfonated xanthene to the conjugated substance $S_c$. Selected examples of functional groups and linkages are shown in Table 2, where the reaction of an electrophilic group and a nucleophilic group yields a covalent linkage.

TABLE 2

Examples of some routes to useful covalent linkages

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |

TABLE 2-continued

Examples of some routes to useful covalent linkages

| Electrophilic Group | Nucleophilic Group | Resulting Covalent Linkage |
|---|---|---|
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carboxylic acids | amines/anilines | carboxamides |
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols | thioethers |
| haloacetamides | thiols | thioethers |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g. succinimidyloxy (—O$C_4H_4O_2$) sulfosuccinimidyloxy (—O$C_4H_3O_2$—$SO_3H$), -1-oxybenzotriazolyl (—O$C_6H_4N_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCO$R^a$ or —OCN$R^a$NH$R^b$, where $R^a$ and $R^b$, which may be the same or different, are $C_1$–$C_6$ alkyl, $C_1$–$C_6$ perfluoroalkyl, or $C_1$–$C_6$ alkoxy; or cyclohexyl, 3-dimethylaminopropyl, or N-morpholinoethyl).

**Acyl azides can also rearrange to isocyanates

The covalent linkage L binds the reactive group $R_x$ or conjugated substance $S_c$ to the fluorophore, either directly (L is a single bond) or with a combination of stable chemical bonds, optionally including single, double, triple or aromatic carbon-carbon bonds, as well as carbon-nitrogen bonds, nitrogen-nitrogen bonds, carbon-oxygen bonds, carbon-sulfur bonds, phosphorus-oxygen bonds, and phosphorus-nitrogen bonds. L typically includes ether, thioether, carboxamide, sulfonamide, urea, urethane or hydrazine moieties. Preferred L moieties have 1–20 nonhydrogen atoms selected from the group consisting of C, N, O, P, and S; and are composed of any combination of ether, thioether, amine, ester, carboxamide, sulfonamide, hydrazide bonds and aromatic or heteroaromatic bonds. Preferably L is a combination of single carbon-carbon bonds and carboxamide or thioether bonds. The longest linear segment of the linkage L preferably contains 4–10 nonhydrogen atoms, including one or two heteroatoms. Examples of L include substituted or unsubstituted polymethylene, arylene, alkylarylene, arylenealkyl, or arylthio. In one embodiment, L contains 1–6 carbon atoms; in another, L is a thioether linkage. In yet another embodiment, L is or incorporates the formula $-(CH_2)_a(CONH(CH_2)_b)_z-$, where a has any value from 0–5, b has any value from 1–5 and z is 0 or 1.

The $-L-R_x$ and $-L-S_c$ moieties are bound directly to the fluorophore at any of $R^2-R^5$ or $R^7-R^{16}$, preferably at one of $R^{13}-R^{16}$, more preferably at $R^{14}$ or $R^{15}$, or is present as a substituent on an alkyl, alkoxy, alkylthio or alkylamino substituent. In one embodiment, exactly one of $R^2$, $R^3$, $R^4$, $R^5$, $R^7$, $R^9$, $R^{10}$, $R_{11}$, $R^{12}$, $R^{13}$, $R^{14}$, $R^{15}$ or $R^{16}$ is an $-L-R_x$ or $-L-S_c$ moiety. In another embodiment, exactly one of $R^{13}$, $R^{14}$, $R^{15}$, or $R^{16}$ is an $-L-R_x$ or $-L-S_c$ moiety. In one embodiment, exactly one of $R^{13}$, $R^{14}$, $R^{15}$ and $R^{16}$ is an $-L-R_x$ or $-L-S_c$ moiety. In another embodiment, exactly one of $R^2$, $R^3$, $R^4$, $R^5$, $R^7$, $R^8$, $R^9$ or $R^{10}$ is an $-L-R_x$ or $-L-S_c$ moiety.

Choice of the reactive group used to attach the fluorophore to the substance to be conjugated typically depends on the functional group on the substance to be conjugated and the type or length of covalent linkage desired. The types of functional groups typically present on the organic or inorganic substances include, but are not limited to, amines, thiols, alcohols, phenols, aldehydes, ketones, phosphates, imidazoles, hydrazines, hydroxylamines, disubstituted amines, halides, epoxides, sulfonate esters, purines, pyrimidines, carboxylic acids, or a combination of these groups. A single type of reactive site may be available on the substance (typical for polysaccharides), or a variety of sites may occur (e.g. amines, thiols, alcohols, phenols), as is typical for proteins. A conjugated substance may be conjugated to more than one fluorophore, which may be the same or different, or to a substance that is additionally modified by a hapten, such as biotin. Although some selectivity can be obtained by careful control of the reaction conditions, selectivity of labeling is best obtained by selection of an appropriate reactive dye.

Typically, $R_x$ will react with an amine, a thiol, an alcohol, an aldehyde or a ketone. In one embodiment, $R_x$ is an acrylamide, an activated ester of a carboxylic acid, an acyl azide, an acyl nitrile, an aldehyde, an alkyl halide, an amine, an anhydride, an aniline, an aryl halide, an azide, an aziridine, a boronate, a carboxylic acid, a diazoalkane, a haloacetamide, a halotriazine, a hydrazine (including hydrazides), an imido ester, an isocyanate, an isothiocyanate, a maleimide, a phosphoramidite, a sulfonyl halide, or a thiol group. Preferably, $R_x$ is a carboxylic acid, a succinimidyl ester, an amine, a haloacetamide, a hydrazine, an isothiocyanate, a maleimide group or an azidoperfluorobenzamido group.

Where the reactive group is a photoactivatable group, such as an azide, diazirinyl or azidoaryl derivative, the dye becomes chemically reactive only after illumination with light of an appropriate wavelength.

Where $R_x$ is a succinimidyl ester of a carboxylic acid, the reactive dye is particularly useful for preparing dye-conjugates of proteins or oligonucleotides. Where $R_x$ is a maleimide, the reactive dye is particularly useful for conjugation to thiol-containing substances. Where $R_x$ is a hydrazide, the reactive dye is particularly useful for conjugation to periodate-oxidized carbohydrates and glycoproteins, and in addition is an aldehyde-fixable polar tracer for cell microinjection.

The reactive dyes of the invention are useful for the preparation of any conjugated substance that possess a suitable functional group for covalent attachment of the fluorophore. Examples of particularly useful dye-conjugates include, among others, conjugates of antigens, steroids, vitamins, drugs, haptens, metabolites, toxins, environmental pollutants, amino acids, peptides, proteins, nucleic acids, nucleic acid polymers, carbohydrates, lipids, ion-complexing moieties, and non-biological polymers. Alternatively, these are conjugates of cells, cellular systems, cellular fragments, or subcellular particles. Examples include, among others, virus particles, bacterial particles, virus components, biological cells (such as animal cells, plant cells, bacteria, yeast, or protists), or cellular components. Sulfonated reactive dyes typically label reactive sites at the cell surface, in cell membranes, organelles, or cytoplasm. Preferably the conjugated substance is an amino acid, peptide, protein, tyramine, polysaccharide, ion-complexing moiety, nucleotide, nucleic acid polymer, hapten, drug, hormone, lipid, lipid assembly, polymer, polymeric microparticle, biological cell or virus. In one embodiment, conjugates of biological polymers such as peptides, proteins, oligonucleotides, nucleic acid polymers are also labeled with a second fluorescent or non-fluorescent dye, including an additional dye of the present invention, to form an energy-transfer pair.

In one embodiment, the conjugated substance ($S_c$) is an amino acid (including those that are protected or are substituted by phosphates, carbohydrates, or $C_1$ to $C_{22}$ carboxylic acids), or is a polymer of amino acids such as a peptide or protein. Preferred conjugates of peptides contain at least five amino acids, more preferably 5 to 36 amino acids. Preferred peptides include, but are not limited to, neuropeptides, cytokines, toxins, protease substrates, and protein kinase substrates. Preferred protein conjugates include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the conjugated protein is an antibody, an antibody fragment, avidin, streptavidin, a toxin, a lectin, a hormone, or a growth factor. Typically where the conjugated substance is a toxin, it is a neuropeptide or a phallotoxin, such as phalloidin.

In another embodiment, the conjugated substance ($S_c$) is a nucleic acid base, nucleoside, nucleotide or a nucleic acid polymer, including those that were modified to possess an additional linker or spacer for attachment of the dyes of the invention, such as an alkynyl linkage (U.S. Pat. No. 5,047,519), an aminoallyl linkage (U.S. Pat. No. 4,711,955) or other linkage. Preferably, the conjugated nucleotide is a nucleoside triphosphate or a deoxynucleoside triphosphate or a dideoxynucleoside triphosphate.

Preferred nucleic acid polymer conjugates are labeled, single- or multi-stranded, natural or synthetic DNA or RNA, DNA or RNA oligonucleotides, or DNA/RNA hybrids, or incorporate an unusual linker such as morpholine derivatized phosphates (AntiVirals, Inc., Corvallis Oreg.), or peptide nucleic acids such as N-(2-aminoethyl)glycine units. When the nucleic acid is a synthetic oligonucleotide, it typically contains fewer than 50 nucleotides, more typically fewer than 25 nucleotides. Larger fluorescent nucleic acid polymers are typically prepared from labeled nucleotides or oligonucleotides using oligonucleotide-primed DNA polymerization, such as by using the polymerase chain reaction or through primer extension, or by terminal-transferase catalyzed addition of a labeled nucleotide to a 3'-end of a nucleic acid polymer. Typically, the dye is attached via one or more purine or pyrimidine bases through an amide, ester, ether or thioether bond; or is attached to the phosphate or carbohydrate by a bond that is an ester, thioester, amide, ether or thioether. Alternatively, dye conjugate of the invention is simultaneously labeled with a hapten such as biotin or digoxigenin, or to an enzyme such as alkaline phosphatase, or to a protein such as an antibody. Nucleotide conjugates of the invention are readily incorporated by DNA polymerase and can be used for in situ hybridization (Example 54) and nucleic acid sequencing (e.g., U.S. Pat. Nos. 5,332,666; 5,171,534; and 4,997,928; and WO Appl. 94/05688).

In another embodiment, the conjugated substance ($S_c$) is a carbohydrate that is typically a polysaccharide, such as a dextran, FICOLL, heparin, glycogen, amylopectin, mannan, inulin, starch, agarose and cellulose. Alternatively, the carbohydrate is a polysaccharides that is a lipopolysaccharide. Preferred polysaccharide conjugates are dextran or FICOLL conjugates.

In another embodiment, the conjugated substance ($S_c$), is a lipid (typically having 6–60 carbons), including glycolipids, phospholipids, sphingolipids, and steroids. Alternatively, the conjugated substance is a lipid assembly, such as a liposome. The lipophilic moiety may be used to retain the conjugated substances in cells, as described in U.S. Pat. No. 5,208,148.

Conjugates having an ion-complexing moiety serve as indicators for calcium, sodium, magnesium, potassium, or other biologically important metal ions. Preferred ion-complexing moieties are crown ethers, including diaryldiaza crown ethers (U.S. Pat. No. 5,405,975); BAPTA chelators (U.S. Pat. Nos. 5,453,517, 5,516,911, and 5,049,673); APTRA chelators (AM. J. PHYSIOL. 256, C540 (1989)); or pyridine- and phenanthroline-based metal ion chelators (U.S. Pat. No. 5,648,270). Preferably the ion-complexing moiety is a diaryldiaza crown ether or BAPTA chelator. The ion indicators are optionally conjugated to plastic or biological polymers such as dextrans or microspheres to improve their utility as sensors. Alternatively, where the dye is a fluorescein or a rhodol, the dye itself acts as an indicator of $H^+$ at pH values within about 1.5 pH units of the individual dye's pKa.

Other conjugates of non-biological materials include dye-conjugates of organic or inorganic polymers, polymeric films, polymeric wafers, polymeric membranes, polymeric particles, polymeric microparticles including magnetic and non-magnetic microspheres, conducting and non-conducting metals and non-metals, and glass and plastic surfaces and particles. Conjugates are optionally prepared by copolymerization of a sulfonated dye that contains an appropriate functionality while preparing the polymer, or by chemical modification of a polymer that contains functional groups with suitable chemical reactivity. Other types of reactions that are useful for preparing dye-conjugates of polymers include catalyzed polymerizations or copolymerizations of alkenes and reactions of dienes with dienophiles, transesterifications or transaminations. In another embodiment, the conjugated substance is a glass or silica, which may be formed into an optical fiber or other structure.

The preparation of dye conjugates using reactive dyes is well documented, e.g. by R. Haugland, MOLECULAR PROBES HANDBOOK OF FLUORESCENT PROBES AND RESEARCH CHEMICALS, Chapters 1–3 (1996); and Brinkley, BIOCONJUGATE CHEM., 3, 2 (1992). Conjugates typically result from mixing appropriate sulfonated reactive dyes and the substance to be conjugated in a suitable solvent in which both are soluble. The dyes of the invention are readily soluble in aqueous solutions, facilitating conjugation reactions with most biological materials. For those reactive dyes that are photoactivated, conjugation requires illumination of the reaction mixture to activate the reactive dye.

Labeled members of a specific binding pair are typically used as fluorescent probes for the complementary member of that specific binding pair, each specific binding pair member having an area on the surface or in a cavity that specifically binds to and is complementary with a particular spatial and polar organization of the other. Preferred specific binding pair members are proteins that bind non-covalently to low molecular weight ligands, such as biotin, drug-haptens and fluorescent dyes (such as an anti-fluorescein antibody). Such probes optionally contain a covalently bound moiety that is removed by an enzyme or light, or $R^{11}$ is H and the compound fluoresces following oxidation. Representative specific binding pairs are shown in Table 3.

TABLE 3

Representative Specific Binding Pairs

| antigen | antibody |
|---|---|
| biotin | avidin (or streptavidin or anti-biotin) |
| IgG* | protein A or protein G |
| drug | drug receptor |
| toxin | toxin receptor |
| carbohydrate | lectin or carbohydrate receptor |
| peptide | peptide receptor |
| protein | protein receptor |
| enzyme substrate | enzyme |
| DNA (RNA) | aDNA (aRNA)† |
| hormone | hormone receptor |
| ion | chelator |

*IgG is an immunoglobulin
†aDNA and aRNA are the antisense (complementary) strands used for hybridization In another embodiment of the invention, the sulfonated xanthene dye is substituted by a blocking moiety that substantially alters the fluorescence of the fluorophore, where the subsequent removal of the blocking moiety restores the fluorescence of the parent dye. Typically, cleavage of the blocking moiety from the dye is accomplished by enzymatic activity, making the blocked dye an enzyme substrate (for example as described by Mangel et al., U.S. Pat. No. 4,557,862 (1985)). Alternatively, the blocking moiety is a photolabile caging group, such as a substituted or unsubstituted derivative of o-nitroarylmethine (including α-carboxy o-nitroarylmethine (U.S. Pat. No. 5,635,608 to Haugland et al. (1997)) and bis-(5-t-butoxycarbonylmethoxy)-2-nitrobenzyl), of 2-methoxy-5-nitrophenyl, or of desyl.

Enzymes that may be detected or quantitated using appropriately blocked dyes include microsomal dealkylases (for example, cytochrome P450 enzymes), glycosidases (for example β-galactosidase, β-glucosidase, α-fucosidase, β-glucosaminidase), phosphatases, sulfatases, esterases, lipases, guanidinobenzoatases and others. Conjugates of rhodol dyes that are amino acid or peptide amides are typically useful as peptidase substrates. Where the sulfonated xanthene is conjugated to a tyramine molecule, the resulting dye-conjugate is useful as a substrate for peroxidase enzymes (as described in U.S. Pat. No. 5,196,306 to Bobrow et al. (1993)). The reduced derivatives of xanthylium dyes (i.e., those of Formula II wherein $R^{11}$ is H) serve as substrates for enzymes that take up electrons, or in the detection of chemical oxidizing agents, reactive oxygen species or nitric oxides. Sulfonation of the xanthene dyes provides improved water solubility for these substrates.

Applications and Methods of Use

The dye compounds of the invention are generally utilized by combining a sulfonated xanthene dye compound as described above with the sample of interest under conditions selected to yield a detectable optical response. The term "dye compound" is used herein to refer to all aspects of the claimed sulfonated xanthene dyes, including both reactive and non-reactive sulfonated xanthenes and conjugates of sulfonated xanthenes. The dye compound typically forms a covalent or non-covalent association or complex with an element of the sample, or is simply present within the bounds of the sample or portion of the sample. The sample is then illuminated at a wavelength selected to elicit the optical response. Typically, staining the sample is used to determine a specified characteristic of the sample by further comparing the optical response with a standard or expected response.

For biological applications, the dye compounds of the invention are typically used in an aqueous, mostly aqueous or aqueous-miscible solution prepared according to methods generally known in the art. The exact concentration of dye compound is dependent upon the experimental conditions and the desired results, but typically ranges from about one nanomolar to one millimolar or more. The optimal concentration is determined by systematic variation until satisfactory results with minimal background fluorescence is accomplished.

The dye compounds are most advantageously used to stain samples with biological components. The sample may comprise heterogeneous mixtures of components (including intact cells, cell extracts, bacteria, viruses, organelles, and mixtures thereof), or a single component or homogeneous group of components (e.g. natural or synthetic amino acid, nucleic acid or carbohydrate polymers, or lipid membrane complexes). These dyes are generally non-toxic to living cells and other biological components, within the concentrations of use, although those sulfonated dyes that are additionally substituted one or more times by Br or I are efficient photosensitizers.

The dye compound is combined with the sample in any way that facilitates contact between the dye compound and the sample components of interest. Typically, the dye compound or a solution containing the dye compound is simply added to the sample. More so than other xanthene derivatives, sulfonated xanthene derivatives tend to be impermeant to membranes of biological cells, but once inside viable cells are typically well retained. Treatments that permeabilize the plasma membrane, such as electroporation, shock treatments or high extracellular ATP can be used to introduce dye compounds into cells. Alternatively, the dye compounds are physically inserted into cells, e.g. by pressure microinjection, scrape loading, patch clamp methods, or phagocytosis.

Sulfonated xanthene dyes that incorporate an amine or a hydrazine residue can be microinjected into cells, where they can be fixed in place by aldehyde fixatives such as formaldehyde or glutaraldehyde. This fixability makes such dyes useful for intracellular applications such as neuronal tracing.

Solubilization of the fluorophore in water by the sulfonate moieties and their relative impermeance to membranes gives the dye compounds of the invention particular utility as polar tracers, according to methods generally known in the art for other dye compounds, see e.g. U.S. Pat. No. 4,473,693 to Stewart (1984) (using lucifer yellow) and U.S. Pat. No. 5,514,710 to Haugland et al. (1996) (using caged hydroxypyrenesulfonic acids) (both patents incorporated by reference). Nonsulfonated xanthenes are not suitable for such applications because they are typically not well retained in living cells, whereas the high photostability, enhanced solubility and high extinction coefficients of the dyes of the present invention make them superior reagents for these applications.

Dye compounds that possess a lipophilic substituent, such as phospholipids, will non-covalently incorporate into lipid assemblies, e.g. for use as probes for membrane structure; or for incorporation in liposomes, lipoproteins, films, plastics, lipophilic microspheres or similar materials; or for tracing. Lipophilic sulfonated xanthene dyes are useful as fluorescent probes of membrane structure, wherein the sulfonic acid moiety permits trapping of the probe at or near the membrane's surface.

Chemically reactive dye compounds will covalently attach to a corresponding functional group on a wide variety of materials, forming dye conjugates as described above. Using dye compounds to label reactive sites on the surface of cells, in cell membranes or in intracellular compartments such as organelles, or in the cell's cytoplasm, permits the determination of their presence or quantity, accessibility, or their spatial and temporal distribution in the sample. The relative impermeance of the dyes of the invention to membranes of biological cells, give them utility as fluorescent probes for assessing the topography of protein distribution in living cells, or as an indicator of single cell viability (Example 55). Photoreactive sulfonated xanthene dyes can be used similarly to photolabel components of the outer membrane of biological cells or as photo-fixable polar tracers for cells. Outside of the cellular milieu, the negative charge of the dye compounds at neutral pH also facilitates the electrophoretic separation of dye-conjugates of carbohydrates, drugs and other low molecular weight compounds for analysis by capillary zone electrophoresis (CZE), HPLC or other separation techniques. Precipitation of the conjugate is minimized, even after labeling with multiple fluorophores, since the sulfonated xanthene derivatives are fully ionized at neutral pH.

Optionally, the sample is washed after staining to remove residual, excess or unbound dye compound. The sample is optionally combined with one or more other solutions in the course of staining, including wash solutions, permeabilization and/or fixation solutions, and solutions containing additional detection reagents. An additional detection reagent typically produces a detectable response due to the presence of a specific cell component, intracellular substance, or cellular condition, according to methods generally known in the art. Where the additional detection reagent has, or yields a product with, spectral properties that differ from those of the subject dye compounds, multi-color applications are possible. This is particularly useful where the additional detection reagent is a dye or dye-conjugate of the present invention having spectral properties that are detectably distinct from those of the staining dye.

The compounds of the invention that are dye conjugates are used according to methods extensively known in the art; e.g. use of antibody conjugates in microscopy and immunofluorescent assays; and nucleotide or oligonucleotide conjugates for nucleic acid hybridization assays and nucleic acid sequencing (e.g., U.S. Pat. Nos. 5,332,666 to Prober, et al. (1994); 5,171,534 to Smith, et al. (1992); 4,997,928 to Hobbs (1991); and WO Appl. 94/05688 to Menchen, et al.; all incorporated by reference). Dye-conjugates of multiple independent dyes of the invention possess utility for multicolor applications.

Dye-conjugates of antibodies to fluorophores possess utility for amplification of fluorescence. For example, the sulfonated rhodamine dyes of the invention exhibit no crossreactivity with anti-fluorescein. The use of antifluorescein antibodies conjugated to green fluorescent sulfonated xanthene dyes to amplify fluorescein labels results in both amplification of signal and photostabilization, due to the high photostability of the dyes of the present invention. Labeled antibodies are also useful for multi-color applications, as the use of a red fluorescent anti-fluorescein antibody in conjunction with fluorescein labeling results in a bright, photostable red fluorescent signal.

At any time after or during staining, the sample is illuminated with a wavelength of light selected to give a detectable optical response, and observed with a means for detecting the optical response. Equipment that is useful for illuminating the dye compounds of the invention includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors.

A detectable optical response means a change in, or occurrence of, an optical signal that is detectable either by observation or instrumentally. Typically the detectable response is a change in fluorescence, such as a change in the intensity, excitation or emission wavelength distribution of fluorescence, fluorescence lifetime, fluorescence polarization, or a combination thereof. The degree and/or location of staining, compared with a standard or expected response, indicates whether and to what degree the sample possesses a given characteristic.

The optical response is optionally detected by visual inspection, or by use of any of the following devices: CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

Dye Synthesis

Xanthylium dyes are typically prepared by condensation of the appropriate resorcinol or aminophenol with various derivatives of benzoic acid, phthalic acid or phthalic anhydride or sulfobenzoic acid or anhydride, including phthalic anhydride, trimellitic anhydride, nitrophthalic anhydride, polyhalogenated phthalic anhydrides, o-sulfobenzoic anhydride, sulfoterephthalic acid, or with benzaldehydes or with aliphatic dicarboxylic acids or anhydrides such as a succinic anhydride or a glutaric anhydride. This condensation occurs in the presence or absence of various acid catalysts (such as zinc chloride, p-toluenesulfonic acid, sulfuric acid, or methanesulfonic acid). An aqueous workup, typically followed by column chromatography, yields the desired xanthylium dye.

For unsymmetric xanthylium dyes, such as rhodols, unsymmetrical fluoresceins, or unsymmetrical rhodamines, condensation can be performed using one equivalent each of the appropriate substituted or unsubstituted resorcinol or aminophenol with one equivalent of a different resorcinol, aminophenol and with one equivalent of the appropriate phthalic acid derivative or benzaldehyde (as listed above) using acid catalysis (as in Khanna et al., U.S. Pat. No. 4,439,359 (1984) and Haugland et al., U.S. Pat. No. 5,227,487 (1993)). The desired asymmetric xanthylium dye is separated from any unwanted symmetric dye side-product using crystallization or chromatographic techniques well-known in the art.

Unsymmetric xanthylium dyes can also be constructed in a stepwise fashion: A selected resorcinol or aminophenol is condensed with one equivalent of the appropriate phthalic acid derivative or benzaldehyde. The resulting benzophenone derivative is typically isolated, purified and then condensed with one equivalent of a different resorcinol or aminophenol, yielding the asymmetric dye.

Sulfonation of xanthylium dyes is typically carried out by stirring the dye in fuming sulfuric acid (20–30% $SO_3$ content) or concentrated sulfuric acid at an appropriate temperature. Sulfonation occurs either at the 4'- and 5'-positions, if available, or/and at the vinylic methyl groups of the xanthylium if the xanthylium dye is substituted by a vinylic substituent. Sulfonation at the 4'- and 5'-positions of fluorescein derivatives is typically carried out by stirring a solution of the desired fluorescein derivative in fuming sulfuric acid (20–30%). Fluorescein derivatives with electron-donating groups on the xanthylium ring are typically sulfonated at room temperature, while fluorescein derivatives having electron-withdrawing groups such as fluorine and chlorine on the xanthylium ring are typically sulfonated at an elevated temperature, for example at 100–110° C. Mono-sulfonation of rhodol dyes is carried out by stirring the appropriate rhodol dye in fuming sulfuric acid at 0° C. for several hours. Bis-sulfonation of rhodols at both the 4'- and 5'-positions, if available, is achieved by stirring the dye in fuming sulfuric acid at room temperature for several hours. Sulfonation of most rhodamine or rosamine dyes at the 4'- and 5'-positions, if available, is carried out with fuming sulfuric acid at 0° C.; the sulfonation is usually complete as soon as a homogeneous solution is achieved during stirring. Where the xanthylium dye possesses a vinylic methyl group, sulfonation at the vinylic methyl is accomplished by treatment with concentrated sulfuric acid at room temperature. If the 4'- and 5'-positions are also available for sulfonation, sulfonation may occur at those positions as well, provided that fuming sulfuric acid is used as the sulfonating agent.

Post-condensation modifications of xanthylium dyes are well known. For example, the xanthenone portion of the dye can be halogenated by treatment with the appropriate halogenating agent, such as liquid bromine. Xanthenes containing unsaturated fused rings can be hydrogenated to the saturated derivatives. When trimellitic anhydride or its derivatives is used in the dye synthesis, two isomeric carboxylates are typically formed. These isomers are separated or, in most cases, used as the mixture of isomers. The reduced derivatives of xanthylium dyes (i.e., those of Formula II wherein $R^{11}$ is H) are prepared by chemical reduction of the xanthenone portion with zinc dust or borohydride in organic solvents. Similarly to nonsulfonated xanthenes, the amino and hydroxyl groups of sulfonated xanthenes can be acylated or alkylated to yield amides, esters and ethers, some of which are enzyme substrates, caged dyes or fluorescent probes.

The selection of an appropriate polyhalogenated phthalic acid derivative or benzaldehyde in the condensation of the xanthylium dye results in a dye having a tetra- or pentachlorinated or tetra- or pentafluorinated phenyl ring at the 9-position. These polyhaloaryl substituted dyes have been shown to react with thiols via a displacement reaction, and thereby provide a facile method of introducing additional reactive groups (Example 19; and as discussed by Gee, et al. TET. LETT. 37, 7905 (1996)).

The dihydroxanthene and xanthylium versions of the dyes of the invention are freely interconvertible by well-known oxidation or reduction reagents, including borohydrides, aluminum hydrides, hydrogen/catalyst, and dithionites. A variety of oxidizing agents mediate the oxidation of dihydroxanthenes, including molecular oxygen in the presence or absence of a catalyst, nitric oxide, peroxynitrite, dichromate, triphenylcarbenium and chloranil. The xanthenes are also oxidized by enzyme action, including horseradish peroxidase in combination with peroxides or by nitric oxide.

Examples of synthetic strategies for selected sulfonated fluorophores, as well as their characterization, synthetic precursors, conjugates and method of use are given below. The examples below are given so as to illustrate the practice of this invention. They are not intended to limit or define the entire scope of this invention.

EXAMPLES

Example 1

Preparation of Compound 2:

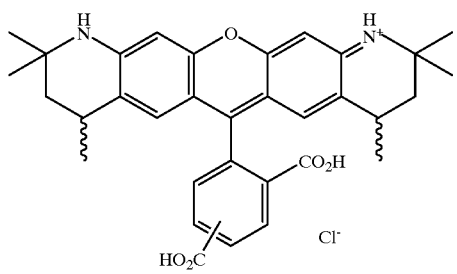

A mixture of 7-hydroxy-2,2,4-trimethyl-1,2,3,4-tetrahydroquinoline (20 g, 74 mmol), trimellitic anhydride (10 g, 52 mmol) and $ZnCl_2$ is heated to 220–230° C. with stirring for 3 hrs. 150 mL water is added to the hot reaction mixture. The resulting precipitate is filtered, washed with water (3×50 mL), and dried. The crude product is purified on silica gel using $MeOH/CHCl_3$. Yield: 10 g.

Example 2

Preparation of Compound 6:

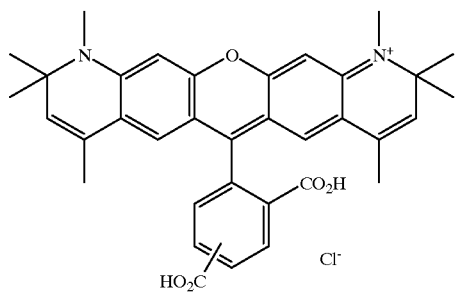

Compound 6 is prepared analogously to Compound 2 (Example 1), only using 7-hydroxy-1,2,2,4-tetramethyl-1,2-dihydroquinoline (15.2 g, 74.9 mmol), trimellitic anhydride (9.35 g, 48.7 mmol) and p-toluenesulfonic acid (1 g) in propionic acid (50 mL). After heating at reflux for 24 hrs, the mixture is poured into 2% HCl (2 L). The crude product is collected, dried and purified by chromatography using $CHCl_3:MeOH=10:1$ to 10:3. (8 g, 36%).

Example 3

Preparation of Compound 8:

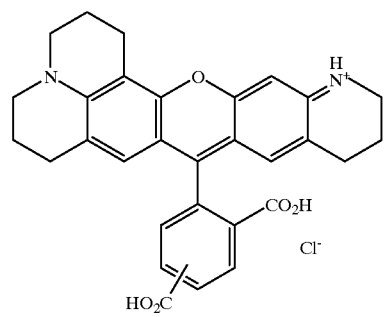

Compound 8 is prepared analogously to Compound 6 (Example 2), only using one equivalent each of 8-hydroxyjulolidine, 7-hydroxy-1,2,3,4-tetrahydroquinoline and trimellitic anhydride.

Example 4

Preparation of Compound 15:

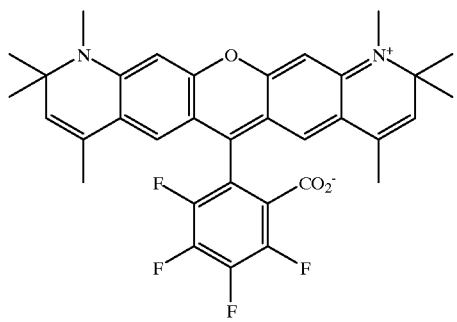

Compound 15 is prepared analogously to Compound 6 (Example 2), using tetrafluorophthalic anhydride in place of trimellitic anhydride.

Example 5
Preparation of Compound 28:

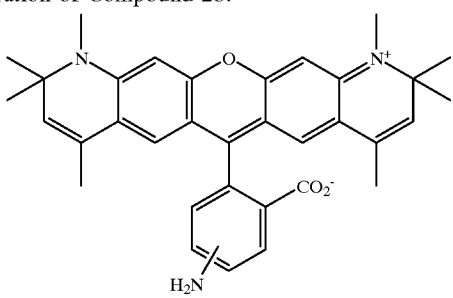

A nitro-substituted analog of Compound 6 is prepared from 7-hydroxy-N-methyl-2,2,4-trimethyl-1,2-dihydroquinoline and 4-nitrophthalic anhydride using the method described in Example 4. Reduction of the nitro group using the method described by McKinney et al. (McKinney, et al. J. ORG. CHEM. 27, 3986 (1962)) gives Compound 28.

Example 6
Preparation of Compound 10:

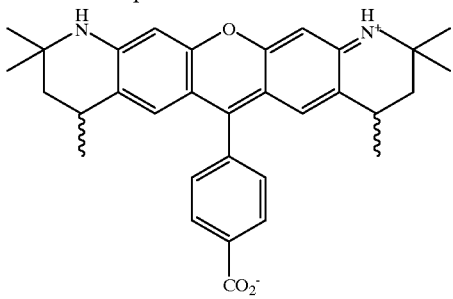

A mixture of 7-hydroxy-1,2,2,4-tetramethyl-1,2,3,4-tetrahydroquinoline hydrobromide (25.8 g, 94.9 mmol) and 4-carboxybenzaldehyde (7.1 g, 47.3 mmol) is stirred in 120 mL 70% $H_2SO_4$ at 130° C. for 4 hrs. The solution is cooled to 0° C. and then neutralized to pH 7 with 70% KOH. The resulting precipitate is filtered, washed with water, and dried. The solid is suspended in 300 mL MeOH and chloranil is added (11.6 g, 47.3 mL). The suspension is heated at reflux for 2 hrs, cooled to room temperature, and rotary evaporated to 100 mL. Ether (500 mL) is added and the precipitate is filtered. The crude product is purified by chromatography on silica gel using MeOH/$CHCl_3$. Yield: 40%.

Example 7
Preparation of Compound 13:

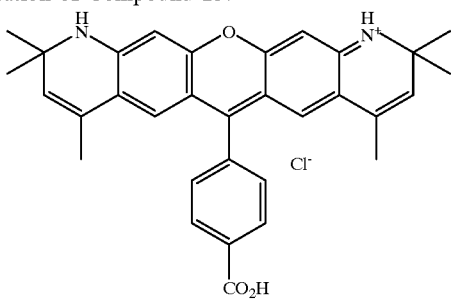

A mixture of 7-hydroxy-2,2,4-trimethyl-1,2-dihydroquinoline (6 g, 22.2 mmol) and 4-carboxybenzaldehyde (2.1 g, 14 mmol) is heated at 150–160° C. with stirring for 6–7 hrs. The mixture is dissolved in MeOH (300 mL), and evaporated to approximately 50 mL, and poured into $Et_2O$ (1.2 L). The crude product is collected and purified by chromatography on silica gel using $CHCl_3$:MeOH=7:3. (2.5 g, 21%).

Example 8
Preparation of Compound 1:

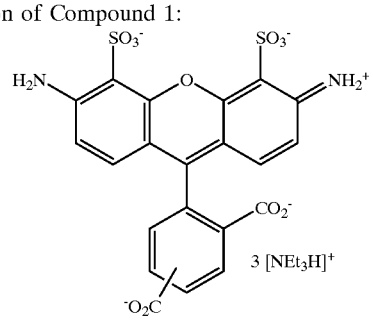

5-(and-6)-Carboxyrhodamine 110, hydrochloride (8.14 g, 19.8 mmol; Molecular Probes, Inc., Eugene, Oreg.) is slowly added in portions to 30% fuming $H_2SO_4$ (50 mL) in an ice bath. After 12 hrs. at 0° C., the solution is poured into 600 mL cold dioxane, and 1.2 L $Et_2O$ is added. The suspension is filtered through diatomaceous earth. The filter cake is suspended in 1.2 L MeOH and the pH is adjusted to ~10 with triethylamine. The mixture is filtered and the filtrate is evaporated. The residue is purified on SEPHADEX LH-20 using water as the eluant to give Compound 1 as an orange solid (9 g).

Example 9
Preparation of Compound 3:

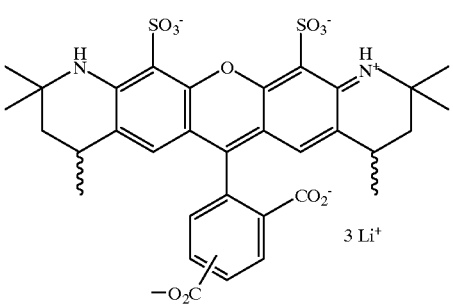

Compound 3 is prepared from Compound 2 using the method described in Example 8 except that LiOH is used to basify the MeOH suspension.

Example 10

Preparation of Compound 9:

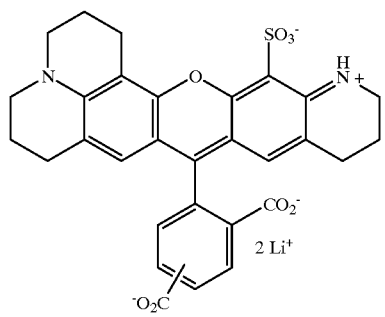

Compound 9 is prepared from Compound 8 using the procedure described in Example 9.

Example 11

Preparation of Compound 11:

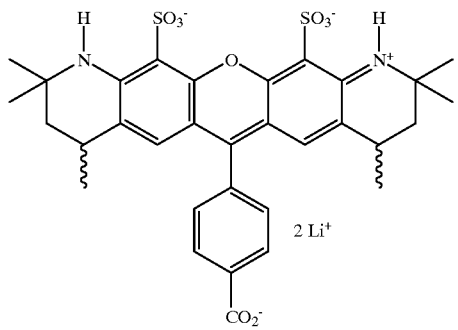

Compound 11 is prepared from Compound 10 using the procedure described in Example 9.

Example 12

Preparation of Compound 17:

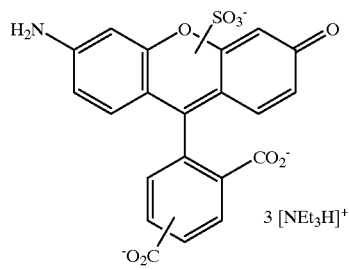

Compound 17 is prepared from 6-amino-9-(2',4'-(or-5')-dicarboxyphenyl)-3H-xanthene-3-one using the procedure described in Example 9. Abs: 493 em (pH 9); Em: 518 nm (pH 9).

Example 13

Preparation of Compound 18:

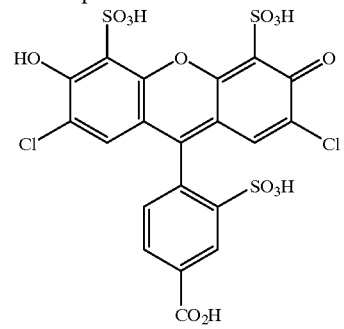

5-Carboxy-2',7'-dichlorosulfonefluorescein (as described in copending application Ser. No. 08/834,008 by Fei Mao, filed Apr. 11, 1997) (1 g, 2.1 mmol) is added to 15 mL 30% fuming $H_2SO_4$. The mixture is heated to 110° C. with stirring for 4 hrs, then cooled to room temperature and poured into ice. The precipitate is filtered then recrystallized from 6% NaCl, giving light yellow crystals. Yield: 70%.

Example 14

Preparation of Compound 7:

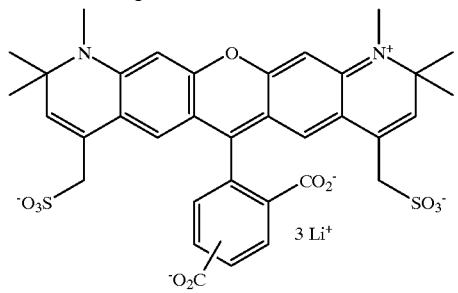

To concentrated $H_2SO_4$ (20 mL) at 0° C. is added Compound 6 (1.7 g, 3.02 mmol). The mixture is stirred at 0° C. for 2 hrs and then at room temperature for 2 days. Dioxane (30 mL) and $Et_2O$ (1 L added. The precipitate is filtered through diatomaceous earth. The filter cake is suspended in $H_2O$ and neutralized with solid $NaHCO_3$. After filtration, the filtrate is evaporated and the residue is purified by chromatography on silica gel (eluant: $CH_3CN:H_2O=8:2$) followed by chromatography on SEPHADEX LH-20 (eluant: $H_2O$). The product is converted to a lithium salt by treatment with lithium cation exchange resin. Yield: 0.7 g (31%).

Example 15

Preparation of Compound 12:

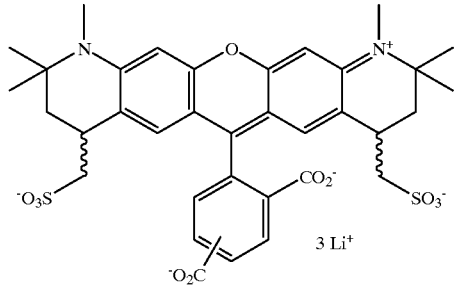

A mixture of Compound 7 (100 mg, 0.14 mmol) and 10% Pd/C (30 mg) in MeOH (10 mL) is hydrogenated at 45 psi overnight. The crude product is purified by chromatography on silica gel using CH$_3$CN:H$_2$O=8:2 as eluant (15 mg, 14%).

Example 16

Preparation of Compound 16:

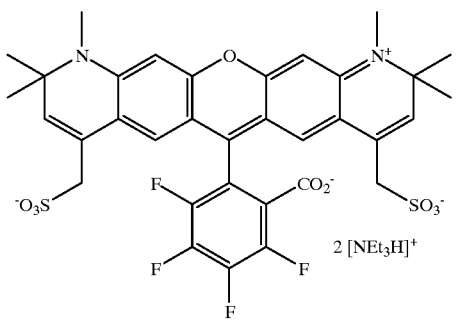

Compound 16 is prepared from Compound 15 using the method described in Example 14.

Example 17

Preparation of Compound 40:

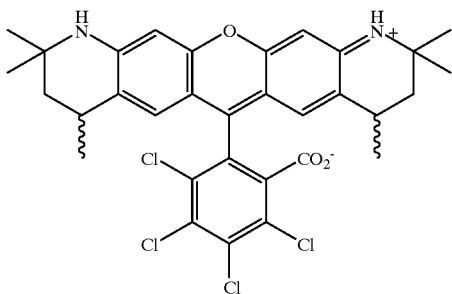

Compound 40 is prepared from tetrachlorophthalic anhydride and 7-hydroxy-2,2,4-trimethyl-1,2,3,4-tetrahydroquinoline using the procedure described in Example 2.

Example 18

Preparation of Compound 41:

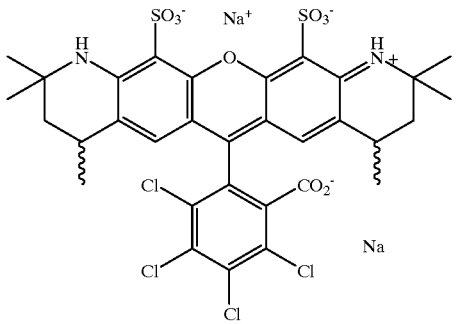

Compound 41 is prepared from Compound 40 and fuming sulfuric acid using the procedure described in Example 8. Abs: 557 (MeOH); Em: 574 nm (MeOH).

Example 19

Preparation of Compound 42:

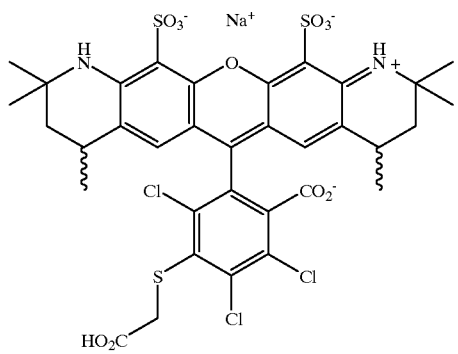

To a solution of Compound 42 (425 mg, 0.54 mmol) in 5 mL DMF under nitrogen is added mercaptoacetic acid (99 mg, 1.07 mmol) and sodium acetate (219 mg, 2.67 mmol). The solution is stirred overnight and then evaporated to dryness in vacuo. The crude product is purified by column chromatography on silica gel eluting with CH$_3$CN:H$_2$O= 85:15. Yield: 79%.

Example 20

Preparation of Compound 14:

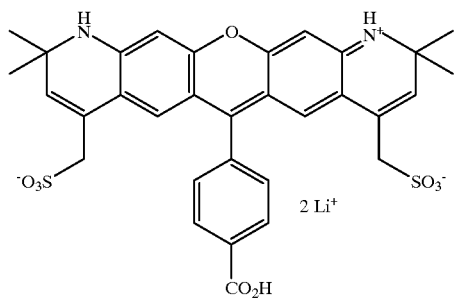

Compound 14 is prepared from Compound 13 using the procedure described in Example 14.

Example 21

Preparation of Compound 30:

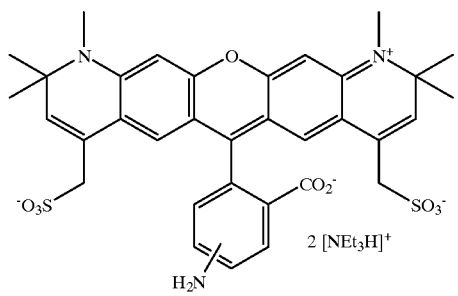

Compound 30 is prepared from Compound 28 using the method described in Example 14.

Example 22
Preparation of Compound 19:

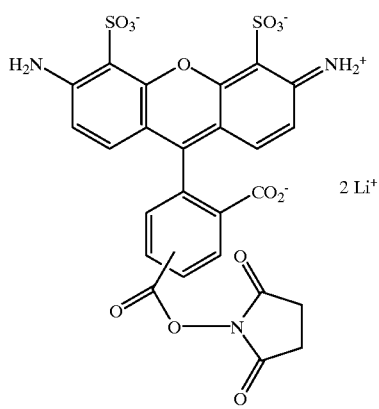

To Compound 1 (200 mg, 0.36 mmol) in 10:4 DMF/H$_2$O (14 mL) at 0° C. is added O-succinimidyl-N,N,N',N'-tetramethyluronium tetrafluoroborate (330 mg, 1.10 mmol) in DMF (6 mL). After 30 minutes at 0° C., the solution is evaporated. The residue is purified by chromatography on silica gel using CH$_3$CN:H$_2$O=8:2 as eluant (60 mg, 26%).

Example 23
Preparation of Compound 20:

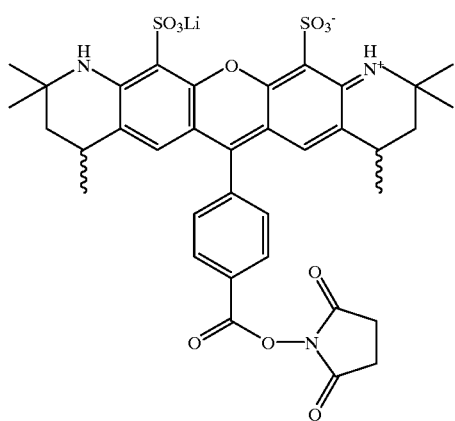

Compound 20 is prepared from Compound 11 using the method described in Example 22. Yield: 80%.

Example 24
Preparation of Compound 21:

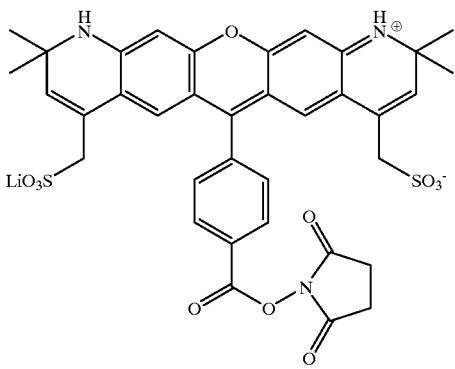

Compound 21 is prepared from Compound 14 using the method described in Example 22.

Example 25
Preparation of Compound 22:

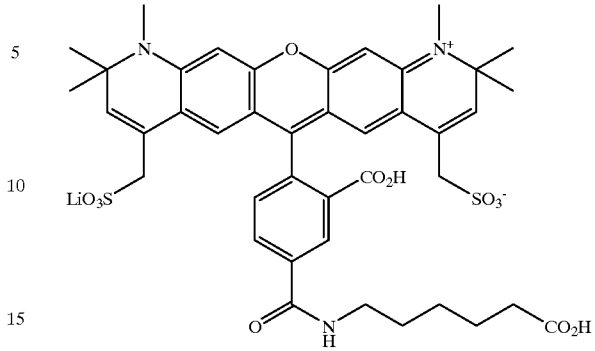

To a solution of the succinimidyl ester of Compound 7 (prepared using the method of Example 22) (17.3 mg, 21.1 mol) in H$_2$O (2 mL) is added aminocaproic acid (5 mg, 38 μmol) followed by 8 drops of N,N-diisopropylethylamine. After 15 minutes the solution is evaporated, and the residue is purified on silica gel using CH$_3$CN:H$_2$O=85:15 as the eluant. The product is treated with Li$^+$ cation exchange resin to give Compound 22 (8 mg).

Example 26
Preparation of Compound 23:

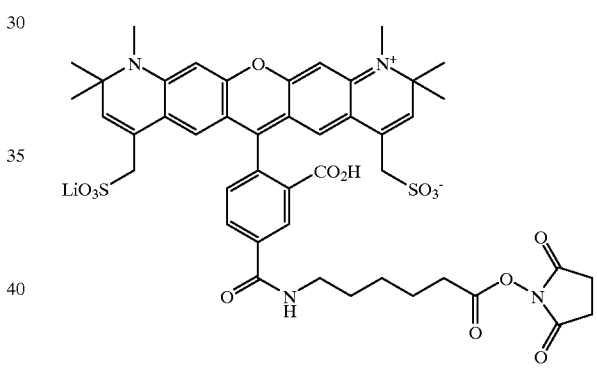

Compound 23 is prepared from Compound 22 using the method described in Example 22.

Example 27
Preparation of Compound 26:

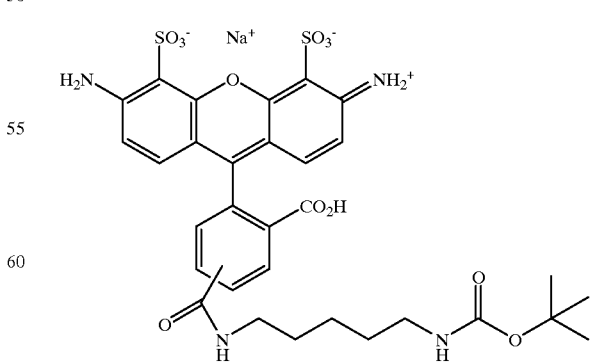

To Compound 19 (100 mg, 0.16 mmol) in H$_2$O (10 mL) is added N-t-BOC-cadaverine (300 mg, 1.58 mmol) in CH₃CN (6 mL). After 45 minutes the mixture is evaporated to dryness. The residue is purified by silica gel chromatography using CH₃CN:H₂O=85:15. The purified compound is dissolved in water and treated with Na⁺ cation exchange resin to give Compound 26 (40 mg, 34%).

Example 28

Preparation of Compound 27:

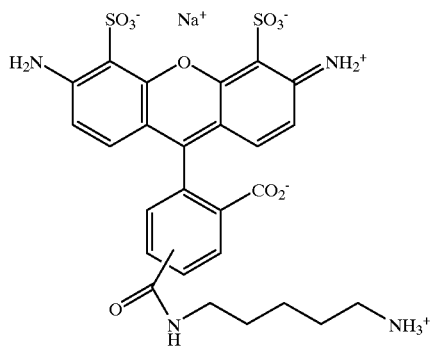

To Compound 26 (300 mg, 0.41 mmol) at 0° C. is added cold trifluoroacetic acid (5 mL). After 15 minutes at 0° C. the mixture is evaporated. The residue is dissolved in CH₃OH (20 mL) and H₂O (30 mL) with Et₃N (2 mL). The solution is evaporated and the residue is purified on SEPHADEX LH-20 to give Compound 27. The Na⁺ salt is prepared using a Na⁺ cation exchange resin.

Example 29

Preparation of Compound 43:

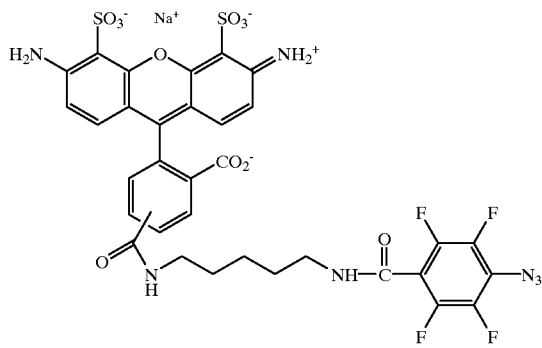

To a solution of equimolar amounts of Compound 27 and triethylamine in DMF is added one equivalent of 4-azido-2,3,5,6-tetrafluorobenzoic acid, succinimidyl ester. After stirring for 4 hours, the reaction mixture is evaporated and the residue purified by silica gel chromatography to give Compound 43.

Example 30

Preparation of Compound 24:

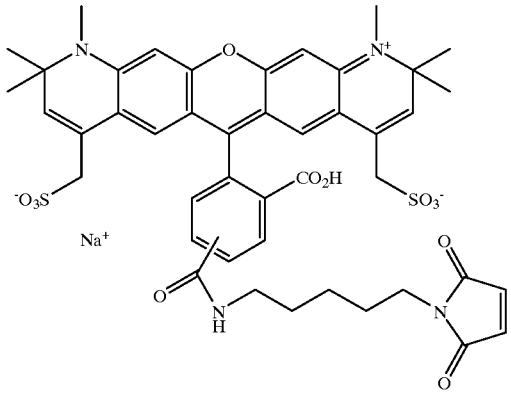

To the succinimidyl ester of Compound 7 (10 mg, 12 μmol) in H₂O is added N-(5-aminopentyl)maleimide trifluoroacetate (5 mg, 17 μmol) in CH₃CN followed by 1 drop of N,N-diisopropylethylamine. After 15 minutes the mixture is evaporated to dryness. The residue is purified by chromatography on silica gel using CH₃CN:H₂O=85:15 then converted to the Na⁺ salt using Na⁺ cation exchange resin giving Compound 24 (6 mg).

Example 31

Preparation of Compound 25:

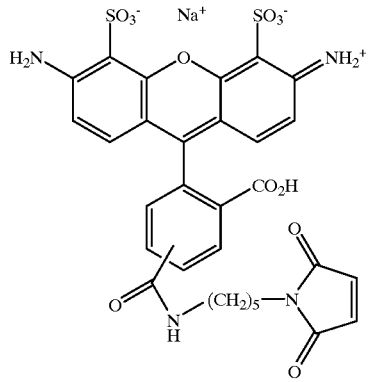

Compound 25 is prepared from Compound 19 using the method described in Example 30.

Example 32

Preparation of Compound 31:

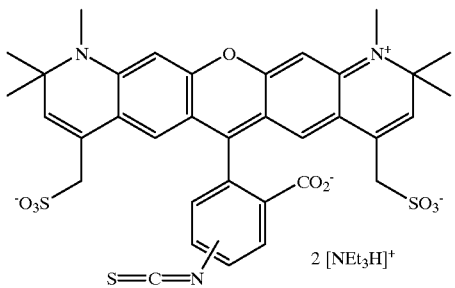

Compound 31 is prepared by treating Compound 30 with excess thiophosgene, using the standard method for isothiocyanate preparation.

Example 33

Preparation of Compound 33:

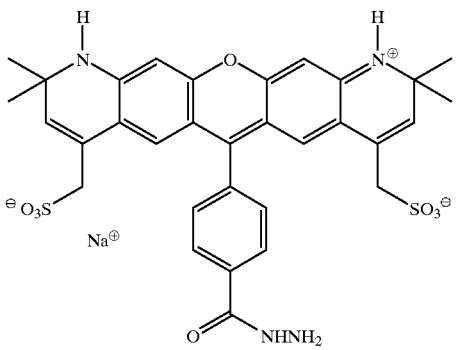

To Compound 21 (0.28 g, 0.37 mmol) in DMF (10 mL) at 0° C. is added t-butyl carbazate (0.15 g, 1.12 mmol). After 30 minutes the solution is evaporated. The intermediate is purified on silica gel using $CH_3CN/H_2O$ (9:1). Trifluoroacetic acid (3 mL) is added, the solution is stirred at 0° C. for 15 min and then evaporated. The product is purified on SEPHADEX LH-20 eluting with $H_2O$. The $Na^+$ salt is prepared by ion exchange using a $Na^+$ cation exchange resin.

Example 34

Preparation of a phalloidin conjugate of a sulfonated rhodamine (Compound 35):

To aminophalloidin p-toluenesulfonate (3.5 mg, 4 μmol) and the succinimidyl ester of Compound 1 (5.0 mg, 5 μmol) in DMF is added N,N-diisopropylethylamine (3 μL, 17 μmol). The mixture is stirred at room temperature for 3 hours. To this is added 7 mL of diethyl ether. The solid is collected by centrifugation. The crude product is purified on SEPHADEX LH-20, eluting with water to give pure Compound 35 (4.0 mg).

Example 35

Preparation of a nucleotide dye-conjugate:

To 2 mg of 5-(3-aminoallyl)-2'-deoxyuridine 5'-triphosphate (Sigma Chemical) in 100 μL water is added 3 mg of Compound 19 in 100 μL DMF and 5 μL triethylamine. After 3 hours, the solution is evaporated and the residue is purified by HPLC. The product fractions are lyophilized to give the green fluorescent nucleotide conjugate (Compound 36).

Alternatively fluorescent dye-conjugates of deoxyuridine 5'-triphosphate are prepared from 5-(3-amino-1-propynyl)-2'-deoxyuridine 5'-triphosphate (as described in Hobbs, Jr. et al, supra).

Example 36

Preparation of an oligonucleotide dye-conjugate

A 5'-amine modified, 18-base M13 primer sequence (~100 μg) is dissolved in 4 μL 0.1 M Tris-EDTA buffer. To this is added 250 μg of Compound 25 (Example 31) in 100 μL 0.1 M sodium borate, pH 8.5. After 16 hours, 10 μL of 5 M NaCl and 3 volumes of cold ethanol are added. The mixture is cooled to −20° C., centrifuged, the supernatant is decanted, the pellet is rinsed with ethanol and then dissolved in 100 μL $H_2O$. The labeled oligonucleotide is purified by HPLC on a 300A C8 reverse-phase column using a ramp gradient of 0.1 M triethylammonium acetate (pH ~7) and acetonitrile (5→45% over 40 min). The desired peak is collected and evaporated to give the fluorescent oligonucleotide.

Example 37

Preparation of a drug dye-conjugate:

A fluorescent dopamine $D_2$ antagonist is prepared as follows: To 10 mg of N-(p-aminophenethyl)spiperone (Amlaiky et al., FEBS LETT 176, 436 (1984)), and 10 μL N,N-diisopropylethylamine in 1 mL of DMF is added 15 mg of Compound 31 (Example 32). After 3 hours, the reaction mixture is poured into 5 mL ether. The precipitate is centrifuged, then purified by chromatography on silica gel using 10–30% methanol in chloroform.

Example 38

Protein conjugates of sulfonated xanthene dyes:

A series of dye conjugates of goat anti-mouse IgG or streptavidin are prepared by standard means (Haugland et al., METH. MOL. BIOL. 45, 205 (1995); Haugland, METH. MOL. BIOL. 45, 223 (1995); Haugland, METH. MOL. BIOL. 45, 235 (1995)) using the reactive succinimidyl esters of the following fluorophores: Compound 1, Compound 4, Compound 5, Compound 7, Compound 14, fluorescein, and CY-3, RHODAMINE GREEN, RHODOL GREEN, RHODAMINE RED-X, AND TEXAS RED-X dyes.

A solution of the desired protein is prepared at 10 mg/mL in 0.1 M sodium bicarbonate. The labeling reagents are dissolved in DMF or water at 10 mg/mL. Predetermined amounts of the labeling reagents are added to the protein solutions with stirring. A molar ratio of 10 equivalents of dye to 1 equivalent of protein is typical, though the optimal amount varies with the particular labeling reagent, the protein being labeled and the protein's concentration, and is determined empirically. The reaction mixture is incubated at room temperature for one hour, or on ice for several hours. The dye-protein conjugate is typically separated from free unreacted reagent by size-exclusion chromatography on CELLUFINE GH-25 equilibrated with PBS. The initial, protein-containing colored band is collected and the degree of substitution is determined from the absorbance at the absorbance maximum of each fluorophore, using the extinction coefficients indicated in Table 4. The absorbance of the dye at 280 nm is subtracted from the total absorbance of the conjugate at 280 nm to get the protein's concentration. Comparison of the absorption of a goat anti-mouse IgG conjugate of Compound 5 (DOS=7) and a goat anti-mouse IgG conjugate of tetramethylrhodamine (DOS=4.3) at the same protein concentration is given in FIG. 1. The conjugate of the present invention exhibits only one absorption peak (545 nm), whereas the tetramethylrhodamine conjugate exhibits two (558 nm and 522 nm). The 522 nm tetramethylrhodamine peak is due to the presence of nonfluorescent rhodamine dimers. The tendency of some rhodamine fluorophores to aggregate at moderate to high levels of dye substitution limits the useful signal that can be obtained from those dye-conjugate

TABLE 4

Extinction Coefficients for selected fluorophores of the invention

| Fluorophore | Extinction Coefficient* $(cm^{-1}mol^{-1})$ |
|---|---|
| Compound 1 | 71,000 |
| Compound 4 | 80,000 |
| Compound 5 | 73,000 |
| Compound 7 | 73,000 |
| Compound 14 | 91,000 |

*Extinction coefficients are determined for the free carboxylic acid in aqueous solution Protein conjugates of antibody fragments, of other avidins and of other proteins are prepared and analyzed similarly.

Example 39

Fluorescent labeling of periodate-oxidized proteins:

Two samples of 5 mg each of goat IgG antibody in 1 mL of 0.1M acetate, 0.135 M NaCl, pH 5.5 are treated with 2.1 mg of sodium metaperiodate on ice, for 1 and 2 hours, respectively. The reactions are stopped by addition of 30 μL ethylene glycol. The antibodies are purified on a MATREX GH 25 column (1 cm×30 cm) packed in PBS pH 7.2. One-tenth volume of 1 M sodium bicarbonate is added to increase the pH and Compound 30 (Example 21) is added at a molar ratio of dye to protein of 100:1. The reaction is stirred for 2 hours at room temperature. Sodium cyanoborohydride is added to a final concentration of 10 mM and the reaction is stirred for 4 hours at room temperature. The antibody conjugates are purified by dialysis and on MATREX GH 25 columns as described above. Antibodies that are oxidized for 1hour typically yield a degree of substitution of 1 mole of dye per mole of IgG. Antibodies that are oxidized for 2 hours yield a degree of substitution of 1.7 mole of dye per mole of IgG.

Example 40

Figure 2:
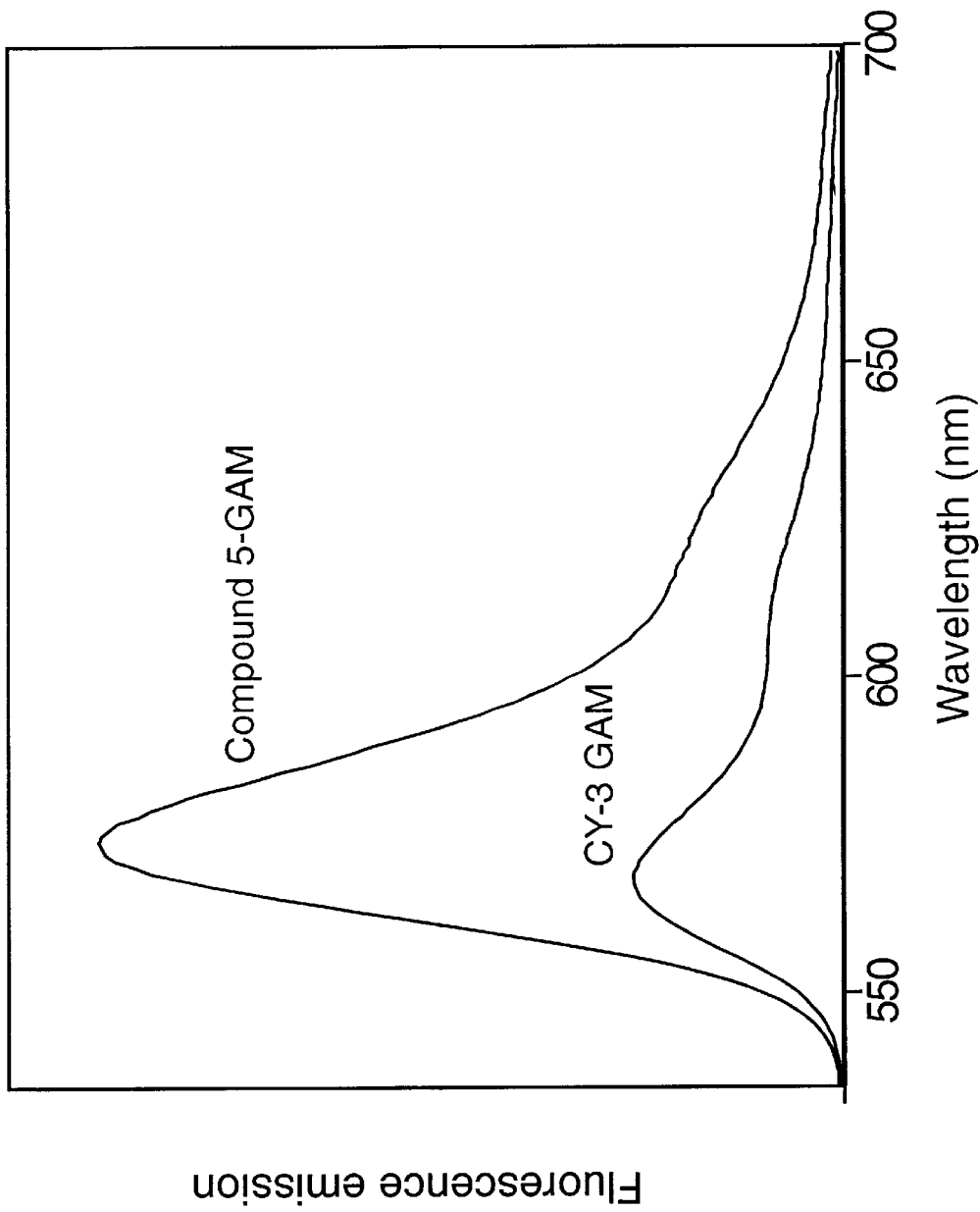
FIG. 2: The fluorescence emission spectra of goat anti-mouse IgG conjugates of Compound 5 (Compound 5-GAM) and CY-3 dye (CY-3 GAM) at similar degrees of substitution and equivalent optical densities, when excited at 530 nm, as described in Example 40.

Total fluorescence of selected dye-protein conjugates as a function of degree of substitution:

A series of goat anti-mouse IgG conjugates is prepared as in Example 39 so as to yield derivatives with similar degrees of substitution (DOS). When measured in a fluorometer, fluorescence of the sulfonated-xanthene dye conjugates is typically higher than that of spectrally similar dyes (Table 5). As shown in FIG. 2, The fluorescence emission spectra of goat anti-mouse IgG conjugates of Compound 5 (DOS 4.0) and CY-3 (DOS 3.8) at the same solution optical densities reveals substantially enhanced fluorescence by the dye-conjugate of the invention, when excited at 530 nm.

mg/mL solution of Compound 24 (Example 30) in DMF. Unreacted dye is removed on a spin column. The degree of substitution by the dye is estimated using $\epsilon=52,600$ $cm^{-1}M^{-1}$ at 595 nm. The protein concentration is estimated from the absorbance at 488 nm, corrected for the absorbance of Compound 24 at that wavelength.

Example 42

Figure 4:
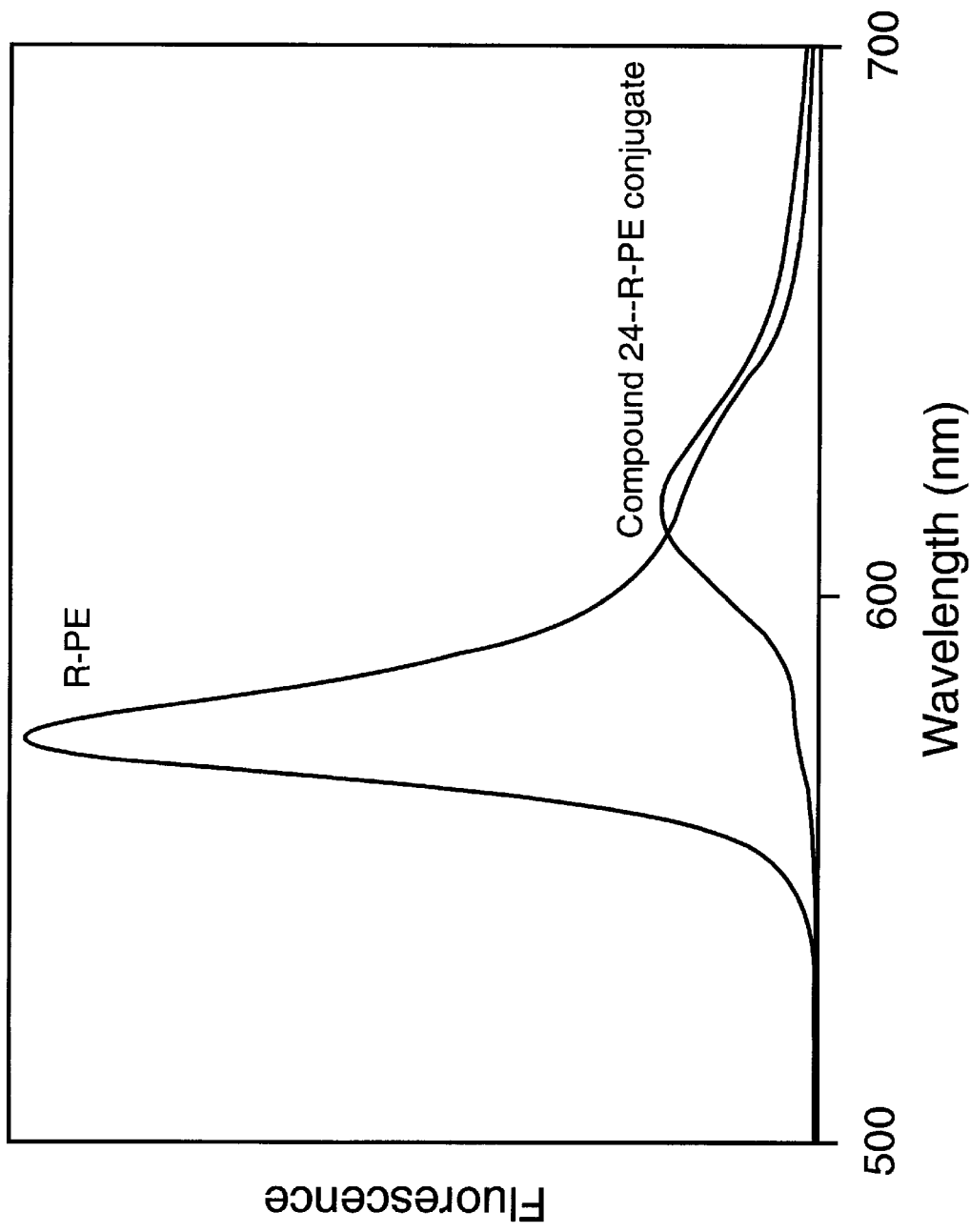
FIG. 4: The fluorescence emission spectra of R-phycoerythrin (R-PE) compared to that of a Compound 24-conjugate of R-phycoerythrin, with excitation at 488 nm, as described in Example 42. Highly efficient energy transfer from the protein to the dye of the invention is demonstrated.

Fluorescence energy transfer in a sulfonated-rhodamine conjugate of R-phycoerythrin:

The R-phycoerythrin conjugate of Example 41 is excited at 488 nm and compared to that of unmodified R-phycoerythrin excited at the same wavelength. FIG. 4 shows highly efficient energy transfer from the protein to the sulfonated rhodamine dye. A conjugate of this complex with streptavidin is prepared essentially as described by Haugland (METH. MOL. BIOL. 45, 205 (1995), supra). This conjugate retains the energy transfer properties and is useful for cell staining in flow cytometers that utilize the argon-ion laser for excitation.

Example 43

Labeling and use of a wheat germ agglutinin dye-conjugate:

Wheat germ agglutinin (170 mg, EY Laboratories) is dissolved in 5 mL $Na_2CO_3$, pH 9.0, containing 14.9 mg N-acetylglucosamine. To this is added 14.8 mg of Compound 19 (Example 22). After 1 hour the solution is purified by gel filtration. A degree of substitution of 2–3 dyes per molecule is determined from the absorption at 490 nm.

A 1 mg/mL stock solution of the resulting wheat germ agglutinin (WGA) conjugate (Compound 37) is prepared in 0.1 M sodium bicarbonate ~pH 8. *Staphylococcus aureus* are cultured for 17 hours at 30° C. in TSB broth. Equal volumes of the TSB culture and a BSA solution (0.25% BSA+0.85% NaCl sterile filtered through 0.2 μM filter) are incubated at

TABLE 5

| Fluorophore | DOS[a] | QY[a] | Comparison Dye | DOS[a] | QY[b] | QY[a]/QY[b] | Fluorescence Standard |
|---|---|---|---|---|---|---|---|
| Compound 1 | 4.3 | 0.69 | OREGON GREEN 488 | 5.0 | 0.53 | 1.3 | Fluorescein |
| Compound 4 | 3.7 | 0.54 | Rhodamine 6G | 3.0 | 0.028 | 19.3 | Rhodamine 6G |
| Compound 5 | 4.0 | 1.25 | CY-3 | 3.8 | 0.466 | 2.68 | tetramethyl-rhodamine |
| Compound 14 | 4.2 | 0.37 | RHODAMINE RED-X | 4.6 | 0.16 | 2.3 | sulforhodamine |
| Compound 7 | 4.7 | 0.47 | TEXAS RED-X | 4.4 | 0.026 | 18.1 | Compound 7 |

[a]Goat anti-mouse IgG conjugate

Figure 3:
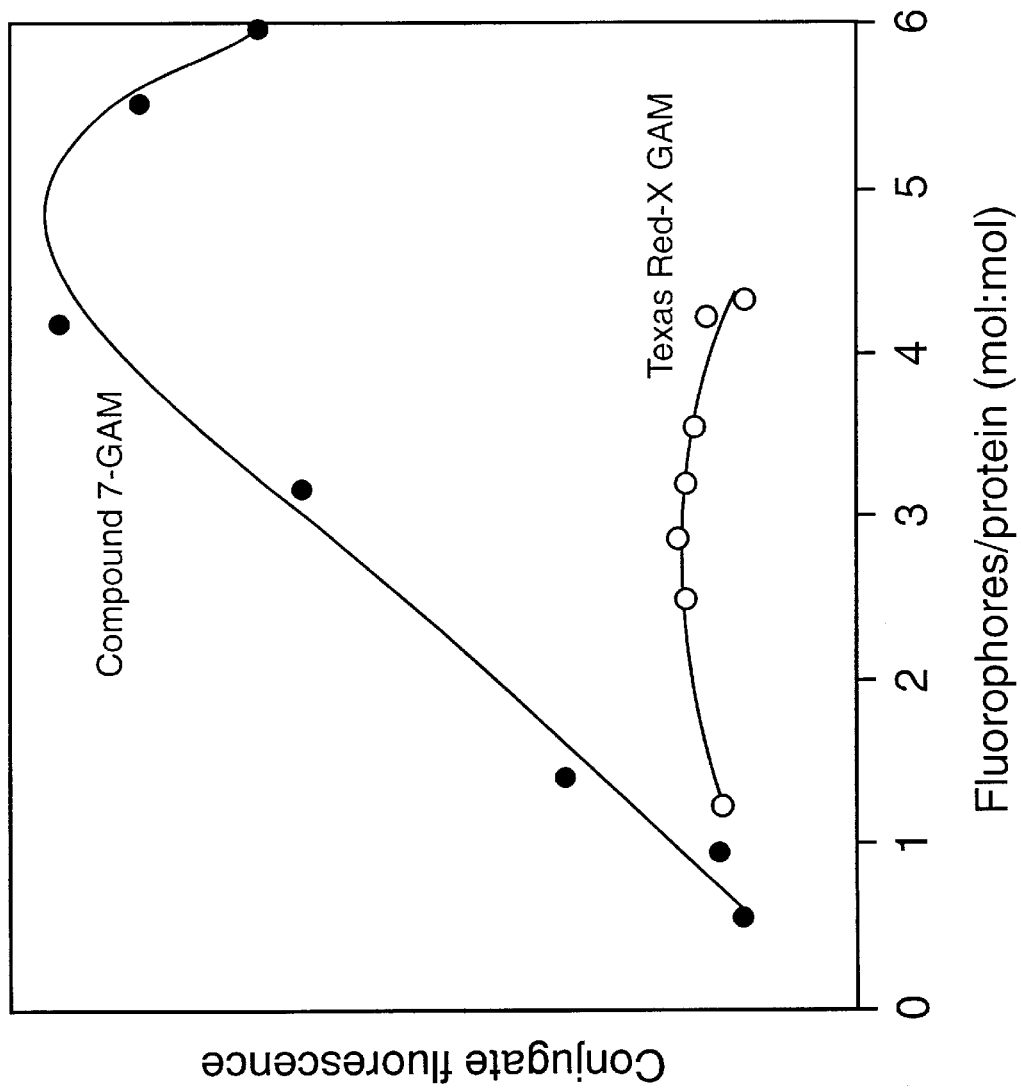
FIG. 3: Conjugate fluorescence vs. degree of substitution for goat anti-mouse IgG conjugates ($F_{ab}2$ fragments) of Compound 7 and TEXAS RED-X dye, showing less quenching at high degrees of substitution for the dyes of the invention, as described in Example 40.

Furthermore, fluorescence of antibody conjugates of Compounds 1, 4, 5, 7, and 14 do not quench appreciably, even at high relatively degrees of substitution (for instance as shown in FIG. 3 for Compound 7 goat anti-mouse IgG conjugate and TEXAS RED-X goat anti-mouse conjugate). Similar results are found with other peptides and proteins, including lectins, protein A, transferrin, fibronectin, enzymes, lipoproteins, glycoproteins and neuropeptides.

Example 41

Labeling R-phycoerythrin with a thiol-reactive sulfonated xanthene dye:

Pyridyldisulfide-modified R-phycoerythrin (Molecular Probes, Inc.), 0.9 mg in 160 μL PBS, pH 7.5, is treated with tris-(2-carboxyethyl)phosphine to reduce the disulfide to a thiol. The thiolated protein is treated with 8 μL of a 20 room temperature for 15 minutes. The BSA-bacterial suspension (200 μL) is centrifuged for 2 minutes at 350 x g, capturing the bacteria on a filter membrane. The cells are resuspended in 90 μL of BSA solution and 10 μL of stain is added for 15 minutes. Following centrifugation, the bacteria are resuspended in BSA solution, and an aliquot is trapped between a slide and a glass coverslip.

The bacteria are observed on a Nikon Diaphot epi-fluorescence microscope using a fluorescein band pass filter set. Images are acquired using the Star-1 cooled CCD camera and the software package supplied with the camera is used for data analysis. Two images are collected for each stain, each image having a 2 sec. exposure time. The intensities of ten individual or pairs of bacteria in each image are analyzed. Bacteria stained with Compound 37 are 1.4 times brighter than bacteria similarly labeled with a fluorescein-WGA conjugate. When used according to Sizemore et al. (U.S. Pat. No. 5,137,810) the conjugate can distinguish between Gram positive and Gram negative bacteria.

Example 44

Simultaneous labeling of actin and tubulin in cultured mammalian cells:

Bovine pulmonary artery cells (BPAEC) are grown to 30–50% confluence on glass. The cells are fixed with 3.7% formaldehyde, permeabilized with 0.2% Triton X-100, and blocked with 6% bovine serum albumin (BSA). All cells are incubated with mouse monoclonal anti-α-tubulin for 60 min. Cells are then washed and divided into two groups for staining.

The first group of cells is labeled with a conjugate of goat anti-mouse IgG and Compound 5 for 30 min, washed, and then incubated with a phalloidin dye-conjugate (Compound 35, Example 33) for an additional 30 min. The second group of cells is labeled with CY-3 conjugated goat anti-mouse IgG for 30 min and then with fluorescein-conjugated phalloidin. Both groups of cells are rinsed with blocking buffer and mounted in phosphate buffered saline (PBS) pH 7.4. Both groups of cells display microtubules decorated with red fluorescence and actin filaments decorated with green fluorescence.

Measurement of photobleaching of the green and red signal on both groups of cells is carried out by exposing the slide to 485 nm excitation (500 dichroic mirror/530 nm bandpass emission filter) continuously for 10 minutes. A similar series of images is acquired with 546 nm excitation (560 nm dichroic mirror/580 nm bandpass emission filter). Green and red cell fluorescence is quantified using software supplied with the CCD camera.

Fluorescein and CY-3 signals from cells mounted in PBS have lower initial intensities and/or more rapid photobleaching than Compound 35 and the anti-mouse conjugate of Compound 5, respectively. Other cellular components are optionally stained with additional dyes having distinguishable spectra. For example, cell nuclei are stained fluorescent blue using DAPI, while other cell antigens are stained deep red fluorescent with antibody conjugates of CY-5.

Example 45

Figure 5:
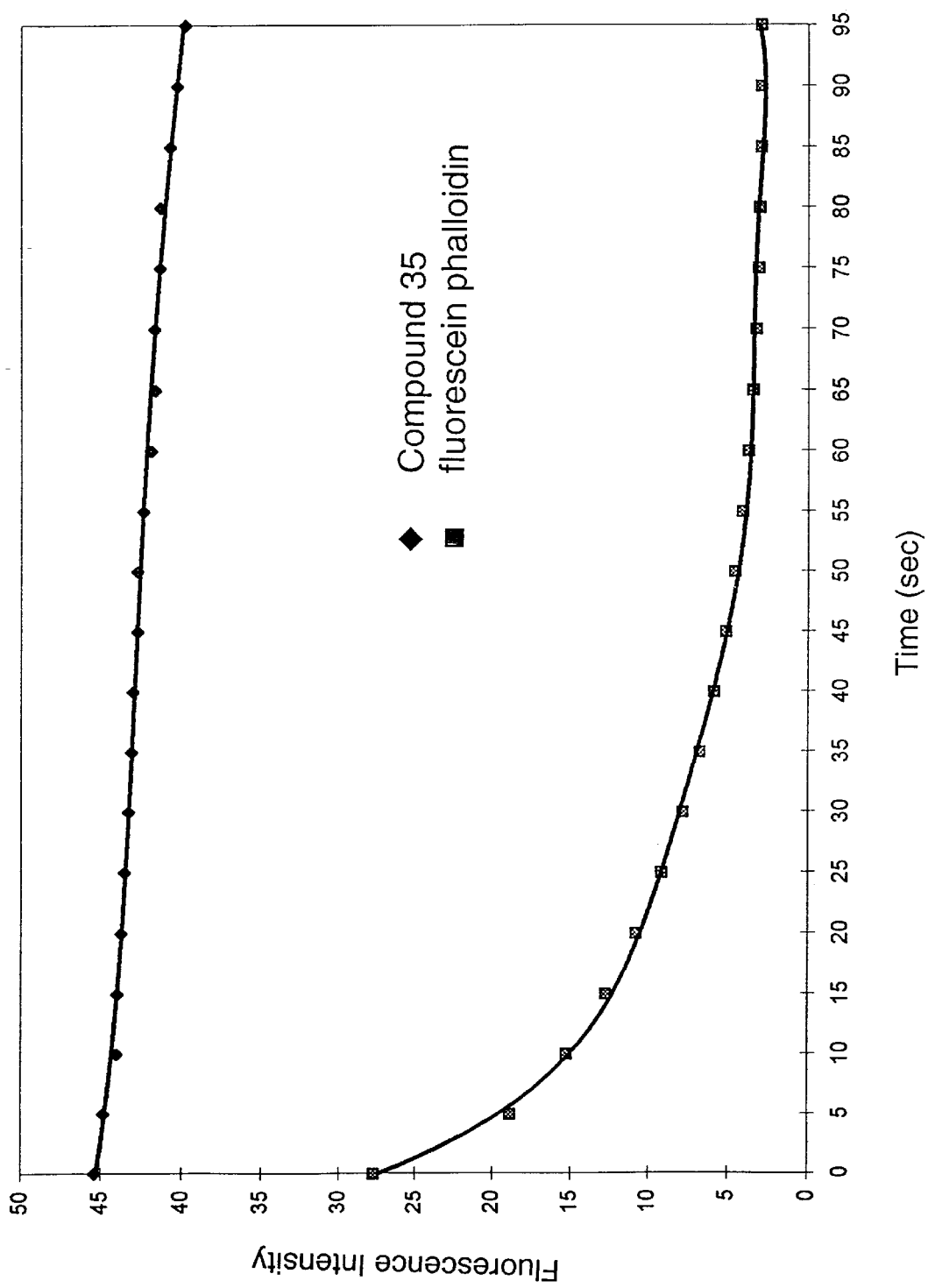
FIG. 5: Relative photobleaching rates of cells stained with a phalloidin conjugate of the present invention (Compound 35) or fluorescein phalloidin, respectively, as described in Example 45. Relative photobleaching rates demonstrate the superior photostability of the dyes of the present invention.

Photobleaching of cells stained with sulfonated xanthene dye-conjugates:

Actin filaments are stained with Compound 35 or fluorescein phalloidin. After washing, each sample is continuously illuminated and viewed on a fluorescence microscope. Relative photobleaching rates, as shown in FIG. 5, clearly demonstrate the superior photostability of the sulfonated rhodamine dye-phalloidin conjugate.

Example 46

Utility of protein dye-conjugates as immunoreagents and resistance to photobleaching:

Antibody conjugates of the dyes in Table 5 are prepared with degrees of substitution of approximately 4–6. INOVA slides are hydrated in 1% bovine serum albumin (BSA) in PBS for 30 minutes. The slide is drained, human autoantibody is applied, the slide is incubated 30 min and rinsed in PBS. Mouse anti-human antibody is applied, the slide is incubated 30 min and rinsed in PBS. Each fluorescent anti-mouse antibody conjugate is applied as a 10 μg/mL solution, diluted in 1% BSA/PBS. After 30 minutes the slides are rinsed in PBS, then in 50 mM Tris pH 8.0, mounted in 50 mM Tris pH 8.0, and viewed through an appropriate filter. All samples give predominantly nuclear staining. Quantitative intensity measurements permit comparison of dyes. Similar results are obtained using a biotinylated anti-mouse preparation and fluorescent streptavidin conjugates.

Figure 6:
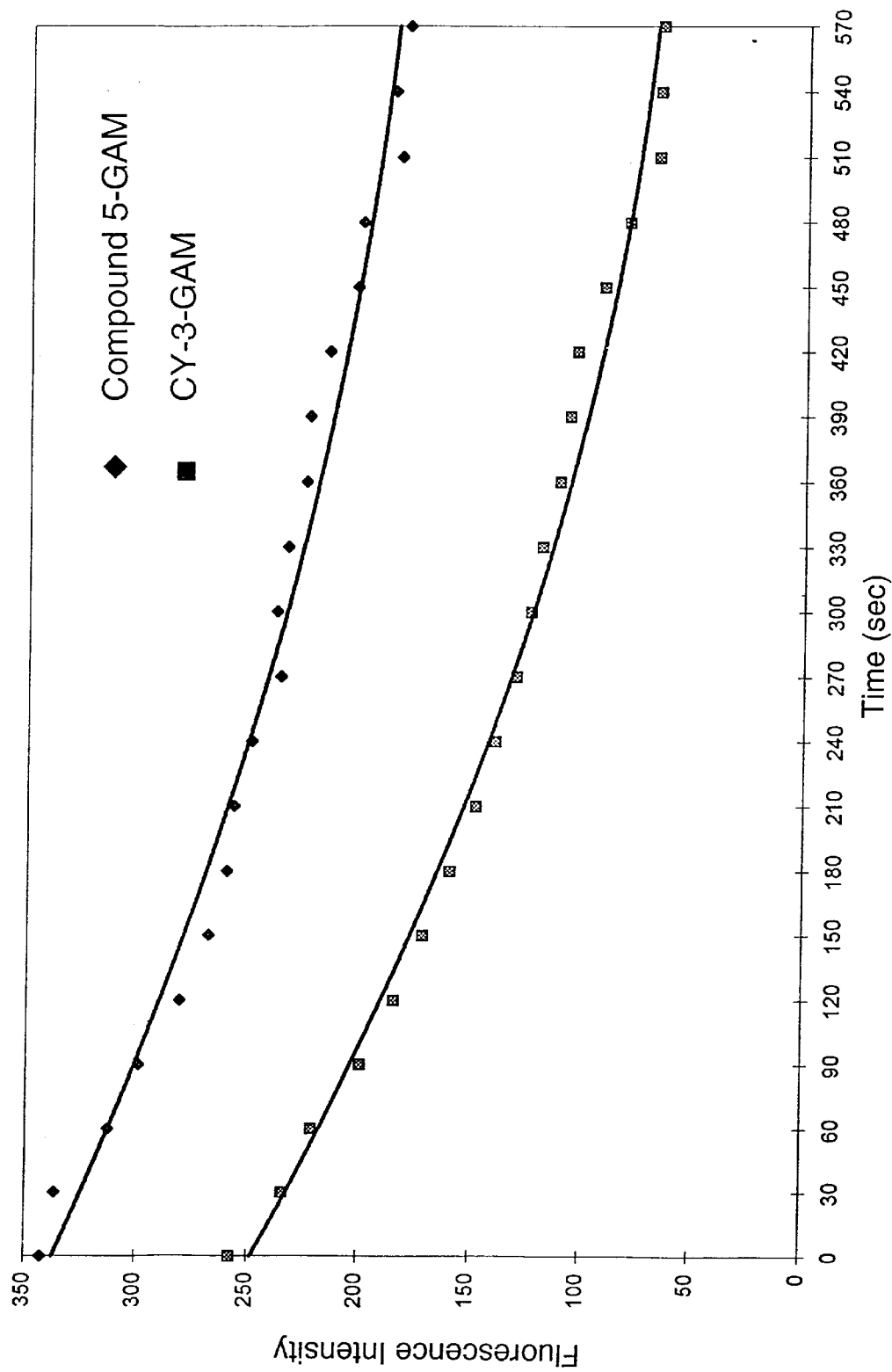
FIG. 6: Relative photobleaching rates of cells stained with goat anti-mouse IgG conjugates of Compound 5 (Compound 5-GAM) and CY-3 dye (CY-3-GAM), as described in Example 45. Relative photobleaching rates demonstrate the superior photostability of the dyes of the present invention

For photobleaching measurements, one image of the slide is acquired every 5 seconds for 100 seconds with continuous illumination. Three fields of cells are bleached, and the photobleaching values are normalized and averaged (FIG. 6). The antibody conjugates of the sulfonated-xanthene dyes are significantly more photostable than other dyes that have comparable spectra, including the CY-3 sulfonated-carbocyanine dye.

Example 47

Preparation and use of a fluorescent α-bungarotoxin dye-conjugate:

α-Bungarotoxin (1 mg) in 25 μL 0.1 M NaHCO$_3$ is treated with 1.5 equivalents of Compound 19 (Example 22) at room temperature for 2 hours. The product is purified by size exclusion and ion exchange chromatography. Staining of acetylcholine receptors and detection of their resulting fluorescence is comparable to that of fluorescein-conjugated α-bungarotoxin, except that the fluorescence of the sulfonated-xanthene dye-conjugate is brighter and more resistant to photobleaching.

Example 48

Preparation of aminodextran dye-conjugates:

70,000 MW aminodextran (50 mg) derivatized with an average of 13 amino groups, is dissolved at 10 mg/mL in 0.1 M NaHCO$_3$. An amine-reactive derivative of the sulfonated-xanthene dye is added so as to give dye/dextran ratio of ~12. After 6 hours the conjugate is purified on SEPHADEX G-50, eluting with water. Typically ~6 moles of dye are conjugated to 70,000 g dextran.

Example 49

Preparation of fluorescent-dye labeled microspheres.

Uniform microspheres are conjugated to sulfonated-xanthene dyes by one of four methods. In Method A, 1.0 μm amine-derivatized polystyrene microspheres are suspended at ~2% solids in 100 mM NaHCO$_3$, pH 8.3 and treated with 2 mg/mL of an amine-reactive sulfonated-xanthene dye. After 1 hour the microspheres are centrifuged and washed with buffer.

In Method B, carboxylate-modified microspheres are suspended in a solution of a protein that has been conjugated to a sulfonated-xanthene dye. Excess protein is removed by centrifugation and washing. Microparticles of a size that cannot be centrifuged are separated from excess protein by dialysis through a semi-permeable membrane with a high MW cutoff or by gel filtration chromatography.

In Method C the protein is covalently coupled through its amine residues to the carboxylate groups of the polymer using ethyl 3-(dimethylaminopropyl)carbodiimide (EDAC).

In Method D, biotinylated microspheres are treated with a streptavidin, avidin or anti-biotin conjugate of a sulfonated-xanthene dye and the conjugates are isolated as in Method B.

The larger particles can be analyzed for uniformity of staining and brightness using flow cytometry. Under a microscope the labeled beads appear as spheres with thin rings at their surface. They are particularly useful for calibration of microscopes, in particular laser-scanning confocal microscopes, and as photostable standards for flow cytometry. The microspheres can be further coupled to proteins, oligonucleotides, haptens and other biomolecules for assays using methods well know in the art. Microspheres labeled with the sulfonated-xanthene dyes appear to be more photostable than those that are surface labeled with other dyes having comparable spectra.

Example 50

Preparation of fluorescent liposomes using the dyes of the invention:

The sulfonated-xanthene dyes of the invention are sufficiently water soluble to be incorporated into the interior of liposomes by methods well known in the art (J. BIOL. CHEM. 257, 13892 (1982) and PROC. NATL. ACAD. SCI. USA 75, 4194 (1978)). Alternatively, liposomes containing sulfonated-xanthenes having a lipophilic substituent (e.g. alkyl having 11–22 carbons), within their membranes are prepared by co-dissolving the fluorescent lipid and the unlabeled phospholipid(s) that make up the liposome before forming the liposome dispersion essentially as described by Szoka, Jr. et al. (ANN. REV. BIOPHYS. BIOENG. 9, 467 (1980)).

Example 51

Preparation of fluorescent dye-conjugates of bacteria:

Heat-killed *Escherichia coli* are suspended at 10 mg/mL in pH 8–9 buffer then incubated with 0.5–1.0 mg/mL of an amine-reactive sulfonated xanthene dye. After 30–60 minutes the labeled bacteria are centrifuged and washed several times with buffer to remove any unconjugated dye. Labeled bacteria that are opsonized are taken up by macrophage, as determined by flow cytometry.

Example 52

Preparing DNA hybridization probes using fluorescent nucleotide dye-conjugates:

For each labeling reaction, a microfuge tube containing about 1 µg of a ~700 bp Hind III - Bgl II fragment of the *E. coli* lacZ structural gene is heated for ~10 minutes at 95° C. to fully separate the strands. The DNA is cooled on ice. A 2 µL of a 2 mg/mL mixture of random sequence hexanucleotides in 0.5 M Tris-HCl, pH 7.2, 0.1 M $MgCl_2$, 1 mM dithiothreitol is added, followed by 2 µL of a dNTP labeling mixture (1 mM dATP, 1 mM dGTP, I mM dCTP, 0.65 mM dTTP and 0.35 mM Compound 36 (Example 35). Sterile distilled, deionized water is added to bring the total volume to 19 µL. 1 µL Klenow DNA polymerase (2 units/µL) is added. The samples are incubated 1 hr at 37° C. The reactions are stopped with 2 µL of 0.2 M EDTA, pH 8.0. The labeled DNA is precipitated with 2.5 µL of 4 M LiCl and 75 µL of −20° C. ethanol. After 2 hours at −20° C. the precipitated nucleic acids are centrifuged at 12,000 rpm. The pellets are washed with cold 70% ethanol, then cold 100% ethanol. The pellets are dried and dissolved in 10 mM Tris-HCl, pH 8.0, 1 mM EDTA. A portion of each sample is analyzed by gel electrophoresis on a 1% agarose minigel under standard conditions. The labeled DNA products are suitable for in situ hybridization experiments for the detection of RNA or DNA, such as is associated with the *E. coli* lacZ gene in cells or tissues.

Example 53

Incorporation of fluorescent nucleotide conjugates into DNA amplification products:

A DNA amplification reaction is prepared as follows: 1 µL each of 20 µM solutions of two oligonucleotide primers that hybridize to the human β-actin gene are added to a labeling reaction containing 5 µL DNA template (100 pmol of a plasmid containing the entire gene), 5 µL 10X reaction buffer (100 mM Tris, pH 8.3, 500 mM KCl), 2.5 µL 1 mM Compound 36 (Example 35), 1 µL 10 mM dATP, 1 µL 10 mM dCTP, 1 µL 10 mM dGTP, 1.5 µL 5 mM dTTP, 3 µL 25 mM $MgCl_2$, and 28 µL distilled, deionized water. The sample is transferred to a thermocycler and processed as follows: one cycle, 94° C., 2.5 minutes; 30 cycles, 94° C., 1 minute, 50° C., 1 minute, 72° C., 1 minute; one cycle, 72° C., 5 minutes; then 4° C. overnight. An aliquot of the sample is mixed with an equal volume of 10% glycerol, loaded onto a 0.9% agarose minigel and electrophoresed. Fluorescent bands of the expected size are visible when the gel is illuminated with 300-nm ultraviolet light.

Example 54

In situ hybridization of an RNA probe:

Mouse fibroblasts are fixed and prepared for mRNA in situ hybridization using standard procedures. A sulfonated-xanthene RNA probe is prepared by in vitro transcription of a plasmid containing the mouse actin structural gene cloned downstream of a phage T3 RNA polymerase promoter. Labeling reactions consist of combining 2 µL DNA template (1 µg DNA), 1 µL each of 10 mM ATP, CTP and GTP, 0.75 µL 10 mM UTP, 2.5 µL 1 mM Compound 36 (Example 35), 2 µL 10X transcription buffer (400 mM Tris, pH 8.0, 100 mM $MgCl_2$, 20 mM spermidine, 100 mM NaCl), 1 µL T3 RNA polymerase (40 units/µL), 1 µL 2 mg/mL BSA, and 8.75 µL water. Reactions are incubated at 37° C. for two hours.

The DNA template is removed by treatment with 20 units DNase I for 15 minutes, at 37° C. The RNA transcript is purified by extraction with an equal volume of phenol:chloroform, 1:1, then by chromatography on SEPHADEX G50. Labeled RNA is denatured for 5 minutes at 50° C., then hybridized to cellular preparations using standard procedures. When preparations are washed and viewed through a fluorescein filter set on a fluorescence microscope, cells expressing actin mRNA show bright green fluorescence.

Example 55

Discrimination of live and dead cells using the dyes of the invention:

Because of the polarity of the sulfonated-xanthene dyes and their relative impermeability through the membranes of live cells, the reactive dyes can be used to discriminate cells that have intact versus compromised cell membranes in a single-color assay as follows:

Mouse monocyte-macrophage, Abelson Leukemia Virus Transformed (RAW264.7) cells are trypsinized and washed with phosphate buffered saline (PBS), pH 7.2. Approximately 8–10 million cells suspended in 180 µL of PBS, pH 7.2 are placed in a glass test tube and heated in a water bath at 50° C. for 20 minutes to kill a fraction of the cells. Approximately 60 µL (2–3 million cells) of the cell suspension is added to 940 µL of PBS, pH 7.2, followed by 0.1 µL of a 1 mg/mL solution of Compound 1 in DMSO. The mixture is incubated on ice for 30 minutes and washed twice with PBS, followed by addition of 200 µL of PBS, pH 7.2, and 2 µL of a 150 µM solution of propidium iodide in water (as a control for discriminating dead cells). Analysis of the cell suspension using flow cytometry shows that the dead cells (as determined by high red fluorescence) have a mean channel fluorescence (MCF) intensity of about 3100 while the live cells have a MCF intensity of about 50.

Example 56

Preparation and use of an anti-dye conjugate to amplify fluorescent labeling:

Polyclonal anti-fluorescein, rabbit IgG (Molecular Probes) is conjugated to Compound 19 essentially as described in Example 38 to give Compound 38. A431 cells are stained with 0.125 μg fluorescein-conjugated epidermal growth factor (fluorescein EGF) by standard methods. After washing twice with 1% BSA in PBS containing 2 mM sodium azide (wash buffer), a portion of the cells are further stained with 3.5 μg of Compound 38. The mixture is incubated on ice for 30 minutes, washed with the wash buffer and analyzed by flow cytometry. Results show an approximate 3-fold amplification in the cell's brightness when amplified using Compound 38 as compared to staining with fluorescein-EGF alone

Example 57

Neuronal tracing using a hydrazide-labeled fluorophore:

Neurons from zebrafish embryos are microinjected with Compound 33 (Example 33), using standard methods as described by Blankenfeld et al. (J. NEUROSCI. METH. 36, 309 (1991)). The neurons rapidly fill with the dye throughout their volume and their red fluorescence is readily observable, even in their finer processes. The staining is fixable in the cells using formaldehyde and standard fixing methods.

It is to be understood that, while the foregoing invention has been described in detail by way of illustration and example, numerous modifications, substitutions, and alterations are possible without departing from the spirit and scope of the invention as described in the following claims.

What is claimed is:

1. A compound having the formula

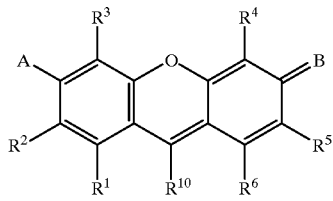

or the formula

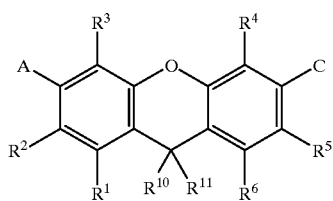

wherein $R^2$, $R^3$, $R^4$ and $R^5$ are independently H, F, Cl, Br, I, CN; or $C_1-C_{18}$ alkyl, or $C_1-C_{18}$ alkoxy, where each alkyl or alkoxy is optionally further substituted by F, Cl, Br, I, a carboxylic acid, a salt of carboxylic acid, or a carboxylic acid ester of a $C_1-C_6$ alcohol; or —$SO_3X$ where X is H or a counterion $R^1$ and $R^6$ are H; or $R^1$ taken in combination with $R^2$, or $R^5$ taken in combination with $R^6$, or both, form a fused aromatic six membered ring that is optionally substituted one or more times by —$SO_3X$;

A is $NR^8R^9$, $R^8$ and $R^9$ are independently H, $C_1-C_6$ alkyl, $C_1-C_6$ carboxyalkyl, $C_1-C_6$ sulfoalkyl, a salt of $C_1-C_6$ carboxyalkyl, or a salt of $C_1-C_6$ sulfoalkyl, wherein the alkyl portions are optionally substituted by amino, hydroxy, carboxylic acid, a salt of carboxylic acid, or a carboxylic acid ester of a $C_1-C_6$ alkyl; or $R^8$ in combination with $R^9$ forms a saturated 5- or 6-membered heterocycle that is a piperidine, a morpholine, a pyrrolidine or a piperazine, each of which is optionally substituted by methyl, carboxylic acid, a salt of carboxylic acid, or a carboxylic acid ester of a $C_1-C_6$ alkyl;

or $R^8$ in combination with $R^2$, or $R^9$ in combination with $R^3$, or both, form a 5- or 6-membered ring that is saturated or unsaturated, and is optionally substituted by one or more $C_1-C_6$ alkyls or —$CH_2SO_3X$ moieties;

C is $OR^{17}$ or $NR^{18}R^{19}$;

where $R^{17}$ is H, or $C_1-C_{18}$ alkyl;

where $R^{18}$ and $R^{19}$ are independently H, $C_1-C_6$ alkyl, $C_1-C_6$ carboxyalkyl, $C_1-C_6$ sulfoalkyl, a salt of $C_1-C_6$ carboxyalkyl, or a salt of $C_1-C_6$ sulfoalkyl, wherein the alkyl portions are optionally substituted by amino, hydroxy, carboxylic acid, a salt of carboxylic acid, or a carboxylic acid ester of a $C_1-C_6$ alkyl; or $R^{18}$ in combination with $R^{19}$ forms a saturated 5- or 6-membered heterocycle that is a piperidine, a morpholine, a pyrrolidine or a piperazine, each of which is optionally substituted by methyl, carboxylic acid, a salt of carboxylic acid, or a carboxylic acid ester of a $C_1-C_6$ alkyl;

or $R^{18}$ in combination with $R^4$, or $R^{19}$ in combination with $R^5$, or both, form a 5- or 6-membered ring that is saturated or unsaturated, and is optionally substituted by one or more $C_1-C_6$ alkyls or —$CH_2SO_3X$ moieties;

B is O or $N^+R^{18}R^{19}$;

$R^{10}$ is H, F, CN, a carboxylic acid, a salt of carboxylic acid, or a carboxylic acid ester of a $C_1-C_6$ alcohol; or $R^{10}$ is a saturated or unsaturated $C_1-C_{18}$ alkyl that is optionally substituted one or more times by F, Cl, Br, carboxylic acid, a salt of carboxylic acid, a carboxylic acid ester of a $C_1-C_6$ alcohol, —$SO_3X$, amino, alkylamino, or dialkylamino, the alkyl groups of which have 1–6 carbons; or $R^{10}$ has the formula

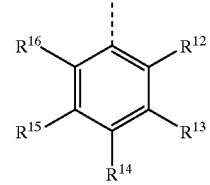

where $R^{12}$, $R^{13}$, $R^{14}$, $R^{15}$ and $R^{16}$ are independently H, F, Cl, Br, I, —$SO_3X$, a carboxylic acid, a salt of carboxylic acid, CN, nitro, hydroxy, azido, amino, hydrazino; or $C_1-C_{18}$ alkyl, $C_1-C_{18}$ alkoxy, $C_1-C_{18}$ alkylthio, $C_1-C_{18}$ alkanoylamino, $C_1-C_{18}$ alkylaminocarbonyl, $C_2-C_{36}$ dialkylaminocarbonyl, $C_1-C_{18}$ alkyloxycarbonyl, or $C_6-C_{18}$ arylcarboxamido, the alkyl or aryl portions of which are optionally substituted one or more times by F, Cl, Br, I, hydroxy, carboxylic acid, a salt of carboxylic acid, a carboxylic acid ester of a $C_1-C_6$ alcohol, —$SO_3X$, amino, alkylamino, dialkylamino or alkoxy, the alkyl portions of each having 1–6 carbons; or one pair of adjacent substituents $R^{13}$ and $R^{14}$, $R^{14}$ and $R^{15}$ or $R^{15}$ and $R^{16}$, when taken in combination, form a fused 6-membered aromatic ring that is optionally further substituted by carboxylic acid, or a salt of carboxylic acid; and $R^{11}$ is H, hydroxy, CN or a $C_1$–$C_6$ alkoxy; or $R^{10}$ in combination with $R^{11}$ forms a 5-membered spirolactone ring or a 5-membered spirosultone ring; or $R^{11}$ in combination with $R^{12}$ forms a 5- or 6-membered spirolactone ring or a 5- or 6-membered spirosultone ring that is optionally and independently substituted by H, F or $CH_3$; or $R^{10}$ when taken in combination with $R^{11}$ is a carbonyl oxygen;

provided that either at least one of $R^2$, $R^3$, $R^4$, and $R^5$ is —$SO_3X$; or $R^8$ in combination with $R^2$, or $R^9$ in combination with $R^3$, or $R^{18}$ in combination with $R^4$, or $R^{19}$ in combination with $R^5$, form a 5- or 6-membered ring that is saturated or unsaturated, and is substituted at a carbon atom by at least one —$CH_2SO_3X$ moiety.

2. A compound, as claimed in claim 1, wherein $R^3$ and $R^4$ are each —$SO_3X$.

3. A compound, as claimed in claim 1, wherein $R^{10}$ has the formula

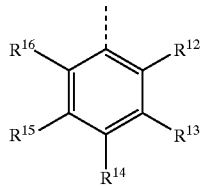

wherein $R^{12}$ is a carboxylic acid, a salt of carboxylic acid, or —$SO_3X$; and $R^{11}$ is not present.

4. A compound, as claimed in claim 3, wherein at least three of $R^{13}$, $R^{14}$, $R^{15}$, and $R^{16}$ are F or Cl.

5. A compound, as claimed in claim 3, wherein one of $R^{14}$ and $R^{15}$ is a carboxylic acid or salt of a carboxylic acid or is —S-$(CH_2)_n$COOH, wherein n is 1–15, and wherein the other of $R^{14}$ or $R^{15}$ is H, F or Cl.

6. A compound, as claimed in claim 1, wherein A is $NR^8R^9$, B is O and C is $OR^{17}$.

7. A compound, as claimed in claim 1, wherein A is $NR^8R^9$, B is $N^+R^{18}R^{19}$, and C is $NR^{18}R^{19}$.

8. A compound, as claimed in claim 7, wherein $R^3$ and $R^4$ are each —$SO_3X$.

9. A compound, as claimed in claim 7, wherein $R^8$ in combination with $R^2$ forms a 5- or 6-membered ring that is saturated or unsaturated, and is optionally substituted by one or more $C_1$–$C_6$ alkyls or —$CH_2SO_3X$ moieties; and $R^{19}$ in combination with $R^5$ forms a 5- or 6-membered ring that is saturated or unsaturated, and is optionally substituted by one or more $C_1$–$C_6$ alkyls or —$CH_2SO_3X$ moieties.

10. A compound, as claimed in claim 9, wherein $R^9$ and $R^{18}$ are independently H, $C_1$–$C_6$ carboxyalkyl, a salt of $C_1$–$C_6$ carboxyalkyl, $C_1$–$C_6$ sulfoalkyl, or a salt of $C_1$–$C_6$ sulfoalkyl.

11. A compound, as claimed in claim 9, wherein $R^8$ in combination with $R^2$, and $R^{19}$ in combination with $R^5$, each form a 5- or 6-membered ring that is saturated; and $R^3$ and $R^4$ are each —$SO_3X$.

12. A compound, as claimed in claim 9, wherein $R^8$ in combination with $R^2$ forms a 5- or 6-membered ring that is saturated or unsaturated, and is substituted by —$CH_2SO_3X$; and $R^{19}$ in combination with $R^5$ forms a 5- or 6-membered ring that is saturated or unsaturated, and is substituted at a carbon atom by —$CH_2SO_3X$.

13. A compound, as claimed in claim 8, wherein $R^1$, $R^2$, $R^5$, and $R^6$ are H;

$R^8$, $R^9$, $R^{18}$, and $R^{19}$ are H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl.

14. A compound, as claimed in claim 1, having the formula

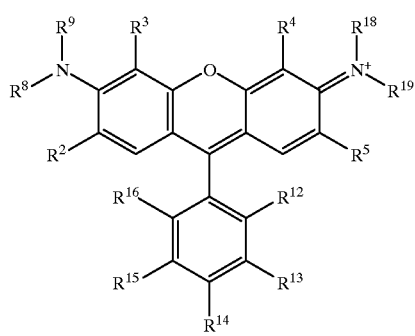

wherein $R^2$, $R^3$, $R^4$ and $R^5$ are independently H, F, Cl, Br, I, $C_1$–$C_{18}$ alkyl, $C_1$–$C_{18}$ alkoxy, or —$SO_3X$;

$R^8$ and $R^9$ are independently H, $C_1$–$C_6$ alkyl, $C_1$–$C_6$ carboxyalkyl, a salt of $C_1$–$C_6$ carboxyalkyl, $C_1$–$C_6$ sulfoalkyl, or a salt of $C_1$–$C_6$ sulfoalkyl; or $R^8$ in combination with $R^2$ forms a 5- or 6-membered ring that is saturated or unsaturated, and that is optionally substituted by one or more $C_1$–$C_6$ alkyls or —$CH_2SO_3X$ moieties;

$R^{18}$ and $R^{19}$ are independently H, $C_1$–$C_6$ alkyl, $C_1$–$C_6$ carboxyalkyl, a salt of $C_1$–$C_6$ carboxyalkyl, $C_1$–$C_6$ sulfoalkyl, or a salt of $C_1$–$C_6$ sulfoalkyl; or $R^{19}$ in combination with $R^5$ forms a 5- or 6-membered ring that is saturated or unsaturated, and that is optionally substituted by one or more $C_1$–$C_6$ alkyls or —$CH_2SO_3X$ moieties;

$R^{12}$, $R^{13}$, $R^{14}$, $R^{15}$ and $R^{16}$ are independently H, Cl, F, amino, nitro, —$SO_3X$, a carboxylic acid, a salt of carboxylic acid, or —S-$(CH_2)_n$COOH where n=1–15;

provided that $R^3$ and $R^4$ are each —$SO_3X$;

or $R^8$ in combination with $R^2$ forms a 5- or 6-membered ring that is saturated or unsaturated, and is substituted —$CH_2SO_3X$; and $R^{19}$ in combination with $R^5$ forms a 5- or 6-membered ring that is saturated or unsaturated, and is substituted at a carbon atom by —$CH_2SO_3X$.

15. A compound having the formula

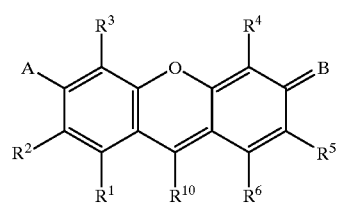

or the formula

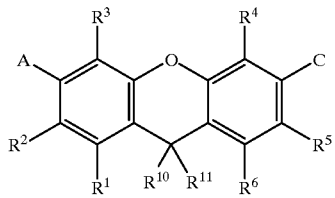

wherein
$R^2$, $R^3$, $R^4$ and $R^5$ are independently H, F, Cl, Br, I, CN; or $C_1$–$C_{18}$ alkyl, or $C_1$–$C_{18}$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol; or —L-$R_x$; or —$SO_3X$ where X is H or a counterion $R^1$ and $R^6$ are H; or $R^1$ taken in combination with $R^2$, or $R^5$ taken in combination with $R^6$, or both, form a fused aromatic six membered ring that is optionally substituted one or more times by —$SO_3X$;

A is $NR^8R^9$, $R^8$ and $R^9$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alkyl; or $R^8$ in combination with $R^9$ forms a saturated 5- or 6-membered heterocycle that is a piperidine, a morpholine, a pyrrolidine or a piperazine, each of which is optionally substituted by methyl, carboxylic acid, a salt of carboxylic acid, or a carboxylic acid ester of a $C_1$–$C_6$ alkyl; or —L-$R_x$;

or $R^8$ in combination with $R^2$, or $R^9$ in combination with $R^3$, or both, form a 5- or 6-membered ring that is saturated or unsaturated, and is optionally substituted by one or more $C_1$–$C_6$ alkyls or —$CH_2SO_3X$ moieties;

C is $OR^{17}$ or $NR^{18}R^{19}$;

where $R^{17}$ is H, or $C_1$–$C_{18}$ alkyl; or —L-$R_x$;

where $R^{18}$ and $R^{19}$ are independently H, $C_1$–$C_6$ alkyl, $C^1$–$C^6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alkyl; or $R^{18}$ in combination with $R^{19}$ forms a saturated 5- or 6-membered heterocycle that is a piperidine, a morpholine, a pyrrolidine or a piperazine, each of which is optionally substituted by methyl, carboxylic acid, a salt of carboxylic acid, or a carboxylic acid ester of a $C_1$–$C_6$ alkyl; or —L-$R_x$;

or $R^{18}$ in combination with $R^4$, or $R^{19}$ in combination with $R^5$, or both, form a 5- or 6-membered ring that is saturated or unsaturated, and is optionally substituted by one or more $C_1$–$C_6$ alkyls or —$CH_2SO_3X$ moieties;

B is O or $N^+R^{18}R^{19}$;

$R^{10}$ is H, F, CN, a carboxylic acid, a salt of carboxylic acid, or a carboxylic acid ester of a $C_1$–$C_6$ alcohol; or $R^{10}$ is a saturated or unsaturated $C_1$–$C_{18}$ alkyl that is optionally substituted one or more times by F, Cl, Br, carboxylic acid, a salt of carboxylic acid, a carboxylic acid ester of a $C_1$–$C_6$ alcohol, —$SO_3X$, amino, alkylamino, or dialkylamino, the alkyl groups of which have 1–6 carbons; or —L-$R_x$; or $R^{10}$ has the formula

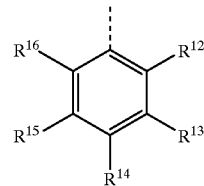

where $R^{12}$, $R^{13}$, $R^{14}$, $R^{15}$ and $R^{16}$ are independently H, F, Cl, Br, I, —$SO_3X$, a carboxylic acid, a salt of carboxylic acid, CN, nitro, hydroxy, azido, amino, hydrazino; or —L-$R_x$; or $C_1$–$C_{18}$ alkyl, $C_1$–$C_{18}$ alkoxy, $C_1$–$C_{18}$ alkylthio, $C_1$–$C_{18}$ alkanoylamino, $C_1$–$C_{18}$ alkylaminocarbonyl, $C_2$–$C_{36}$ dialkylaminocarbonyl, $C_1$–$C_{18}$ alkyloxycarbonyl, or $C_6$–$C_{18}$ arylcarboxamido, the alkyl or aryl portions of which are optionally substituted one or more times by F, Cl, Br, I, hydroxy, carboxylic acid, a salt of carboxylic acid, a carboxylic acid ester of a $C_1$–$C_6$ alcohol, —$SO_3X$, amino, alkylamino, dialkylamino or alkoxy, the alkyl portions of each having 1–6 carbons; or one pair of adjacent substituents $R^{13}$ and $R^{14}$, $R^{14}$ and $R^{15}$ or $R^{15}$ and $R^{16}$, when taken in combination, form a fused 6-membered aromatic ring that is optionally further substituted by carboxylic acid, or a salt of carboxylic acid; and $R^{11}$ is H, hydroxy, CN or a $C_1$–$C_6$ alkoxy; or $R^{10}$ in combination with $R^{11}$ forms a 5-membered spirolactone ring or a 5-membered spirosultone ring; or $R^{11}$ in combination with $R^{12}$ forms a 5- or 6-membered spirolactone ring or a 5- or 6-membered spirosultone ring that is optionally and independently substituted by H, F or $CH_3$; or $R^{10}$ when taken in combination with $R^{11}$ is a carbonyl oxygen;

for all —L-$R_x$, each L is a covalent linkage; and $R_x$ is a reactive group;

provided that either at least one of $R^2$, $R^3$, $R^4$, and $R^5$ is —$SO_3X$; or $R^8$ in combination with $R^2$, or $R^9$ in combination with $R^3$, or $R^{18}$ in combination with $R^4$, or $R^{19}$ in combination with $R^5$, form a 5- or 6-membered ring that is saturated or unsaturated, and is substituted at a carbon atom by at least one —$CH_2SO_3X$ moiety; and that at least one of $R^2$, $R^3$, $R^4$, $R^5$, $R^8$, $R^9$, $R^{10}$, $R^{12}$, $R^{13}$, $R^{14}$, $R^{15}$, $R^{16}$, $R^{17}$, $R^{18}$, and $R^{19}$ is —L-$R_x$.

16. A compound, as claimed in claim 15, wherein each L is independently a single covalent bond, or L is a covalent linkage having 1–24 nonhydrogen atoms selected from the group consisting of C, N, O, P, and S and is composed of any combination of single, double, triple or aromatic carbon-carbon bonds, carbon-nitrogen bonds, nitrogen-nitrogen bonds, carbon-oxygen bonds, carbon-sulfur bonds, phosphorus-oxygen bonds, and phosphorus-nitrogen bonds.

17. A compound, as claimed in claim 15, wherein $R_x$ is an acrylamide, an activated ester of a carboxylic acid, hydroxy, an aldehyde, an alkyl halide, a sulfonate, an amine, an anhydride, an aniline, an aryl halide, an azide, an aziridine, a boronate, a carboxylic acid, a carbodiimide, a diazoalkane, an epoxide, a glycol, a haloacetamide, a halotriazine, a hydrazine, a hydroxylamine, an imido ester, an isocyanate, an isothiocyanate, a ketone, a maleimide, a phosphoramidite, a sulfonyl halide, or a thiol group.

18. A compound, as claimed in claim 15, wherein L is a single covalent bond and $R_x$ is a carboxylic acid, an activated ester of a carboxylic acid, an amine, an azide, a hydrazine, a haloacetamide, an alkyl halide, an isothiocyanate, or a maleimide group.

19. A compound, as claimed in claim 15, wherein $R^2$ and $R^5$ are F or Cl.

20. A compound, as claimed in claim 15, wherein one of $R^{13}$, $R^{14}$, $R^{15}$, and $R^{16}$ is —L-$R_x$.

21. A compound, as claimed in claim 15, wherein one of $R^8$, $R^9$, $R^{17}$, $R^{18}$, and $R^{19}$ is —L-$R_x$.

22. A compound, as claimed in claim 15, wherein A is $NR^8R^9$, B is $N^+R^{18}R^{19}$, and C is $NR^{18}R^{19}$.

23. A compound, as claimed in claim 15, wherein $R^{10}$ has the formula

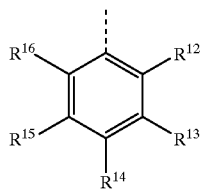

wherein $R^{12}$ is a carboxylic acid, a salt of carboxylic acid, or —$SO_3X$; and $R^{11}$ is not present.

24. A compound, as claimed in claim 23, wherein at least three of $R^{13}$, $R^{14}$, $R^{15}$, and $R^{16}$ are F or Cl.

25. A compound, as claimed in claim 23, wherein one of $R^{14}$ and $R^{15}$ is a carboxylic acid or salt of a carboxylic acid or is —S-$(CH_2)_n$COOH, wherein n is 1–15, and wherein the other of $R^{14}$ or $R^{15}$ is H, F or Cl.

26. A compound, as claimed in claim 15, wherein $R^3$ and $R^4$ are each —$SO_3X$.

27. A compound, as claimed in claim 22, wherein $R^8$ in combination with $R^2$ forms a 5- or 6-membered ring that is saturated or unsaturated, and is optionally substituted by one or more $C_1$-$C_6$ alkyls or —$CH_2SO_3X$ moieties; and $R^{19}$ in combination with $R^5$ forms a 5- or 6-membered ring that is saturated or unsaturated, and is optionally substituted by one or more $C_1$-$C_6$ alkyls or —$CH_2SO_3X$ moieties.

28. A compound, as claimed in claim 27, wherein $R^9$ and $R^{18}$ are independently H, $C_1$-$C_6$ carboxyalkyl, a salt of $C_1$-$C_6$ carboxyalkyl, $C_1$-$C_6$ sulfoalkyl, or a salt of $C_1$-$C_6$ sulfoalkyl.

29. A compound, as claimed in claim 27, wherein $R^8$ in combination with $R^2$, and $R^{19}$ in combination with $R^5$, each form a 5- or 6-membered ring that is saturated; and $R^3$ and $R^4$ are each —$SO_3X$.

30. A compound, as claimed in claim 27, wherein $R^8$ in combination with $R^2$ forms a 5- or 6-membered ring that is saturated or unsaturated, that is substituted by —$CH_2SO_3X$; and $R^{19}$ in combination with $R^5$ forms a 5- or 6-membered ring that is saturated or unsaturated, and is substituted at a carbon atom by —$CH_2SO_3X$.

31. A compound, as claimed in claim 26, wherein $R^1$, $R^2$, $R^5$, and $R^6$ are H;
$R^8$, $R^9$, $R^{18}$, and $R^{19}$ are H, $C_1$-$C_6$ alkyl, $C_1$-$C_6$ carboxyalkyl, $C_1$-$C_6$ sulfoalkyl, a salt of $C_1$-$C_6$ carboxyalkyl, or a salt of $C_1$-$C_6$ sulfoalkyl.

32. A compound, as claimed in claim 15, having the formula

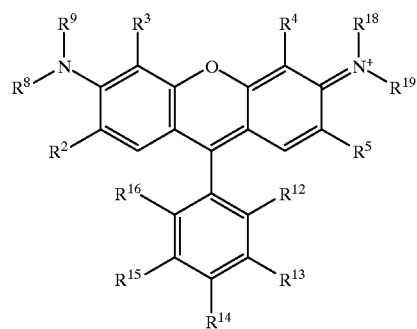

wherein
$R^2$, $R^3$, $R^4$ and $R^5$ are independently H, F, Cl, Br, I; or $C_1$-$C_{18}$ alkyl
$R^8$ and $R^9$ are independently H, $C_1$-$C_6$ alkyl, $C_1$-$C_6$ carboxyalkyl, a salt of $C_1$-$C_6$ carboxyalkyl, $C_1$-$C_6$ sulfoalkyl, or a salt of $C_1$-$C_6$ sulfoalkyl; or $R^8$ in combination with $R^2$ forms a 5- or 6-membered ring that is saturated or unsaturated, and that is optionally substituted by one or more $C_1$-$C_6$ alkyls or —$CH_2SO_3X$ moieties;
$R^{18}$ and $R^{19}$ are independently H, $C_1$-$C_6$ alkyl, $C_1$-$C_6$ carboxyalkyl, a salt of $C_1$-$C_6$ carboxyalkyl, $C_1$-$C_6$ sulfoalkyl, or a salt of $C_1$-$C_6$ sulfoalkyl; or $R^{19}$ in combination with $R^5$ forms a 5- or 6-membered ring that is saturated or unsaturated, and that is optionally substituted by one or more $C_1$-$C_6$ alkyls or —$CH_2SO_3X$ moieties;
$R^{12}$, $R^{13}$, $R^{14}$, $R^{15}$ and $R^{16}$ are independently H, Cl, F, amino, nitro, —$SO_3X$, a carboxylic acid, a salt of carboxylic acid, —S-$(CH_2)_n$COOH where n=1–15, or —L-$R_x$.

33. A compound having the formula

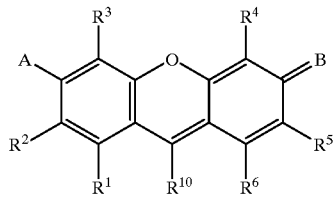

or the formula

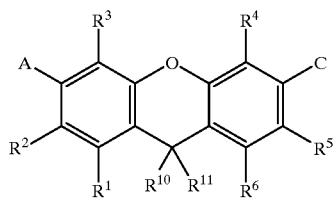

wherein
$R^2$, $R^3$, $R^4$ and $R^5$ are independently H, F, Cl, Br, I, CN; or $C_1$-$C_{18}$ alkyl, or $C_1$-$C_{18}$ alkoxy, where each alkyl or alkoxy is optionally further substituted by F, Cl, Br, I, a carboxylic acid, a salt of carboxylic acid, or a carboxylic acid ester of a $C_1$-$C_6$ alcohol; or —L-$S_c$; or —$SO_3X$ where X is H or a counterion
$R^1$ and $R^6$ are H; or $R^1$ taken in combination with $R^2$, or $R^5$ taken in combination with $R^6$, or both, form a fused aromatic six membered ring that is optionally substituted one or more times by —SO$_3$X;

A is OR$^7$ or NR$^8$R$^9$,

R$^7$ is H, C$_1$–C$_{18}$ alkyl; or —L-S$_c$;

R$^8$ and R$^9$ are independently H, C$_1$–C$_6$ alkyl, C$_1$–C$_6$ carboxyalkyl, C$_1$–C$_6$ sulfoalkyl, a salt of C$_1$–C$_6$ carboxyalkyl, or a salt of C$_1$–C$_6$ sulfoalkyl, wherein the alkyl portions are optionally substituted by amino, hydroxy, carboxylic acid, a salt of carboxylic acid, or a carboxylic acid ester of a C$_1$–C$_6$ alkyl; or R$^9$ in combination with R$^9$ forms a saturated 5- or 6-membered heterocycle that is a piperidine, a morpholine, a pyrrolidine or a piperazine, each of which is optionally substituted by methyl, carboxylic acid, a salt of carboxylic acid, or a carboxylic acid ester of a C$_1$–C$_6$ alkyl; or —L-S$_c$;

or R$^8$ in combination with R$^2$, or R$^9$ in combination with R$^3$, or both, form a 5- or 6-membered ring that is saturated or unsaturated, and is optionally substituted by one or more C$_1$–C$_6$ alkyls or —CH$_2$SO$_3$X moieties;

C is OR$^{17}$ or NR$^{18}$R$^{19}$;

where R$^{17}$ is H, or C$_1$–C$_{18}$ alkyl; or —L-S$_c$;

where R$^{18}$ and R$^{19}$ are independently H, C$_1$–C$_6$ alkyl, C$_1$–C$_6$ carboxyalkyl, C$_1$–C$_6$ sulfoalkyl, a salt of C$_1$–C$_6$ carboxyalkyl, or a salt of C$_1$–C$_6$ sulfoalkyl, wherein the alkyl portions are optionally substituted by amino, hydroxy, carboxylic acid, a salt of carboxylic acid, or a carboxylic acid ester of a C$_1$–C$_6$ alkyl; or R$^{18}$ in combination with R$^{19}$ forms a saturated 5- or 6-membered heterocycle that is a piperidine, a morpholine, a pyrrolidine or a piperazine, each of which is optionally substituted by methyl, carboxylic acid, a salt of carboxylic acid, or a carboxylic acid ester of a C$_1$–C$_6$ alkyl; or —L-S$_c$;

or R$^{18}$ in combination with R$^4$, or R$^{19}$ in combination with R$^5$, or both, form a 5- or 6-membered ring that is saturated or unsaturated, and is optionally substituted by one or more C$_1$–C$_6$ alkyls or —CH$_2$SO$_3$X moieties;

B is O or N$^+$R$^{18}$R$^{19}$;

R$^{10}$ is H, F, CN, a carboxylic acid, a salt of carboxylic acid, or a carboxylic acid ester of a C$_1$–C$_6$ alcohol; or R$^{10}$ is a saturated or unsaturated C$_1$–C$_{18}$ alkyl that is optionally substituted one or more times by F, Cl, Br, carboxylic acid, a salt of carboxylic acid, a carboxylic acid ester of a C$_1$–C$_6$ alcohol, —SO$_3$X, amino, alkylamino, or dialkylamino, the alkyl groups of which have 1–6 carbons; or —L-S$_c$; or R$^{10}$ has the formula

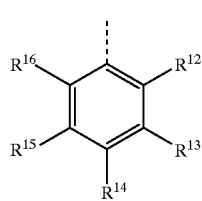

where R$^{12}$, R$^{13}$, R$^{14}$, R$^{15}$ and R$^{16}$ are independently H, F, Cl, Br, I, —SO$_3$X, a carboxylic acid, a salt of carboxylic acid, CN, nitro, hydroxy, azido, amino, hydrazino; or —L-S$_c$; or C$_1$–C$_{18}$ alkyl, C$_1$–C$_{18}$ alkoxy, C$_1$–C$_{18}$ alkylthio, C$_1$–C$_{18}$ alkanoylamino, C$_1$–C$_{18}$ alkylaminocarbonyl, C$_2$–C$_{36}$ dialkylaminocarbonyl, C$_1$–C$_{18}$ alkyloxycarbonyl, or C$_6$–C$_{18}$ arylcarboxamido, the alkyl or aryl portions of which are optionally substituted one or more times by F, Cl, Br, I, hydroxy, carboxylic acid, a salt of carboxylic acid, a carboxylic acid ester of a C$_1$–C$_6$ alcohol, —SO$_3$X, amino, alkylamino, dialkylamino or alkoxy, the alkyl portions of each having 1–6 carbons; or one pair of adjacent substituents R$^{13}$ and R$^{14}$, R$^{14}$ and R$^{15}$ or R$^{15}$ and R$^{16}$, when taken in combination, form a fused 6-membered aromatic ring that is optionally further substituted by carboxylic acid, or a salt of carboxylic acid; and R$^{11}$ is H, hydroxy, CN or a C$_1$–C$_6$ alkoxy; or R$^{10}$ in combination with R$^{11}$ forms a 5-membered spirolactone ring or a 5-membered spirosultone ring; or R$^{11}$ in combination with R$^{12}$ forms a 5- or 6-membered spirolactone ring or a 5- or 6-membered spirosultone ring that is optionally and independently substituted by H, F or CH$_3$; or R$^{10}$ when taken in combination with R$^{11}$ is a carbonyl oxygen;

for all —L-S$_c$, each L is a covalent linkage; and S$_c$ is a conjugated substance;

provided that either at least one of R$^2$, R$^3$, R$^4$, and R$^5$ is —SO$_3$X; or R$^8$ in combination with R$^2$, or R$^9$ in combination with R$^3$, or R$^{18}$ in combination with R$^4$, or R$^{19}$ in combination with R$^5$, form a 5- or 6-membered ring that is saturated or unsaturated, and is substituted at a carbon atom by at least one —CH$_2$SO$_3$X moiety; and that at least one of R$^2$, R$^3$, R$^4$, R$^5$, R$^8$, R$^9$, R$^{10}$, R$^{12}$, R$^{13}$, R$^{14}$, R$^{15}$, R$^{16}$, R$^{18}$, and R$^{19}$ is —L-S$_c$.

34. A compound, as claimed in claim 33, wherein each L is independently a single covalent bond, or L is a covalent linkage having 1–24 nonhydrogen atoms selected from the group consisting of C, N, O, P, and S and is composed of any combination of single, double, triple or aromatic carbon-carbon bonds, carbon-nitrogen bonds, nitrogen-nitrogen bonds, carbon-oxygen bonds, carbon-sulfur bonds, phosphorus-oxygen bonds, and phosphorus-nitrogen bonds.

35. A compound, as claimed in claim 33, wherein S$_c$ is an amino acid, peptide, protein, polysaccharide, ion-complexing moiety, nucleotide, nucleic acid polymer, hapten, drug, lipid, lipid assembly, non-biological organic polymer, polymeric microparticle, animal cell, plant cell, bacterium, yeast, virus or protist.

36. A compound, as claimed in claim 35, wherein S$_c$ is further substituted by one or more additional fluorescent or non-fluorescent dyes.

37. A compound, as claimed in claim 33, wherein S$_c$ is a peptide, protein, polysaccharide, nucleotide, or nucleic acid polymer.

38. A compound, as claimed in claim 33, wherein S$_c$ is an antibody, an avidin, a streptavidin, a lectin, a growth factor, an actin, or a toxin.

39. A compound, as claimed in claim 38, wherein S$_c$ is an antibody to a fluorophore.

40. A compound, as claimed in claim 33, wherein one of R$^{13}$, R$^{14}$, R$^{15}$, and R$^{16}$ is —L-Sc.

41. A compound, as claimed in claim 33, wherein one of R$^7$, R$^8$, R$^9$, R$^{17}$, R$^{18}$, and R$^{19}$ is —L-Sc.

42. A compound, as claimed in claim 33, wherein A is NR$^8$R$^9$, B is N$^+$R$^{18}$R$^{19}$, and C is NR$^{18}$R$^{19}$.

43. A compound, as claimed in claim 33, wherein R$^{10}$ has the formula

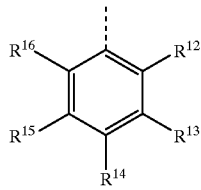

wherein $R^{12}$ is a carboxylic acid, a salt of carboxylic acid, or —$SO_3X$; and $R^{11}$ is not present.

44. A compound, as claimed in claim 43, wherein at least three of $R^{13}$, $R^{14}$, $R^{15}$, and $R^{16}$ are F or Cl.

45. A compound, as claimed in claim 43, wherein one of $R^{14}$ and $R^{15}$ is a carboxylic acid or salt of a carboxylic acid or is —S-$(CH_2)_n$COOH, wherein n is 1–15, and wherein the other of $R^{14}$ or $R^{15}$ is H, F or Cl.

46. A compound, as claimed in claim 33, wherein $R^3$ and $R^4$ are each —$SO_3X$.

47. A compound, as claimed in claim 42, wherein $R^8$ in combination with $R^2$ forms a 5- or 6-membered ring that is saturated or unsaturated, and is optionally substituted by one or more $C_1$–$C_6$ alkyls or —$CH_2SO_3X$ moieties; and $R^{19}$ in combination with $R^5$ forms a 5- or 6-membered ring that is saturated or unsaturated, and is optionally substituted by one or more $C_1$–$C_6$ alkyls or —$CH_2SO_3X$ moieties.

48. A compound, as claimed in claim 47, wherein $R^9$ and $R^{18}$ are independently H, $C_1$–$C_6$ carboxyalkyl, a salt of $C_1$–$C_6$ carboxyalkyl, $C_1$–$C_6$ sulfoalkyl, or a salt of $C_1$–$C_6$ sulfoalkyl.

49. A compound, as claimed in claim 47, wherein $R^8$ in combination with $R^2$, and $R^{19}$ in combination with $R^5$, each form a 5- or 6-membered ring that is saturated; and $R^3$ and $R^4$ are each —$SO_3X$.

50. A compound, as claimed in claim 47, wherein $R^8$ in combination with $R^2$ forms a 5- or 6-membered ring that is saturated or unsaturated, that is substituted by —$CH_2SO_3X$; and $R^{19}$ in combination with $R^5$ forms a 5- or 6-membered ring that is saturated or unsaturated, and is at a carbon atom substituted by —$CH_2SO_3X$.

51. A compound, as claimed in claim 46, wherein $R^1$, $R^2$, $R^5$, and $R^6$ are H; $R^8$, $R^9$, $R^{18}$, and $R^{19}$ are H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl.

52. A compound, as claimed in claim 33, having the formula

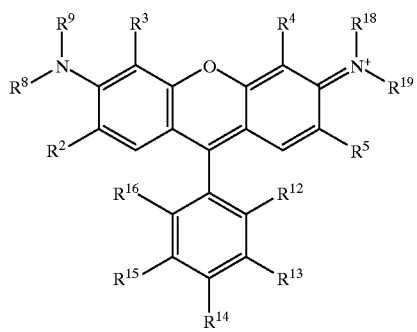

wherein
$R^2$, $R^3$, $R^4$ and $R^5$ are independently H, F, Cl, Br, I, $C_1$–$C_8$ alkyl, $C_1$–$C_{18}$ alkoxy, or —$SO_3X$;
$R^8$ and $R^9$ are independently H, $C_1$–$C_6$ alkyl, $C_1$–$C_6$ carboxyalkyl, a salt of $C_1$–$C_6$ carboxyalkyl, $C_1$–$C_6$ sulfoalkyl, or a salt of $C_1$–$C_6$ sulfoalkyl; or $R^8$ in combination with $R^2$ forms a 5- or 6-membered ring that is saturated or unsaturated, and that is optionally substituted by one or more $C_1$–$C_6$ alkyls or —$CH_2SO_3X$ moieties;
$R^{18}$ and $R^{19}$ are independently H, $C_1$–$C_6$ alkyl, $C_1$–$C_6$ carboxyalkyl, a salt of $C_1$–$C_6$ carboxyalkyl, $C_1$–$C_6$ sulfoalkyl, or a salt of $C_1$–$C_6$ sulfoalkyl; or $R^{19}$ in combination with $R^5$ forms a 5- or 6-membered ring that is saturated or unsaturated, and that is optionally substituted by one or more $C_1$–$C_6$ alkyls or —$CH_2SO_3X$ moieties;
$R^{12}$, $R^{13}$, $R^{14}$, $R^{15}$ and $R^{16}$ are independently H, Cl, F, amino, nitro, —$SO_3X$, a carboxylic acid, a salt of carboxylic acid, or —S-$(CH_2)_n$COOH where n=1–15;
provided that $R^3$ and $R^4$ are each —$SO_3X$;
or
$R^8$ in combination with $R^2$ forms a 5- or 6-membered ring that is saturated or unsaturated, and is substituted by —$CH_2SO_3X$; and $R^{19}$ in combination with $R^5$ forms a 5- or 6-membered ring that is saturated or unsaturated, and is substituted at a carbon atom by —$CH_2SO_3X$.

53. A method of staining a biological sample, comprising: combining a dye solution comprising a compound of the formula

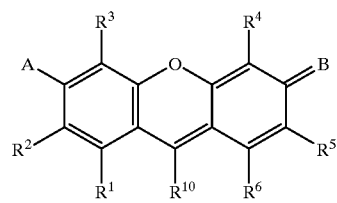

or the formula

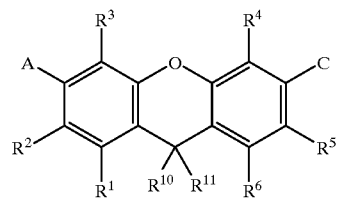

wherein
$R^2$, $R^3$, $R^4$ and $R^5$ are independently H, F, Cl, Br, I, CN; or $C_1$–$C_{18}$ alkyl, or $C_1$–$C_{18}$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol; or —L-$R_x$; —L-$S_c$; or —$SO_3X$ where X is H or a counterion;
$R^1$ and $R^6$ are H; or $R^1$ taken in combination with $R^2$, or $R^5$ taken in combination with $R^6$, or both, form a fused aromatic six membered ring that is optionally substituted one or more times by —$SO_3X$;
A is $OR^7$ or $NR^8R^9$,
$R^7$ is H, $C_1$–$C_{18}$ alkyl; or —L-$R_x$; or —L-$S_c$;
$R^8$ and $R^9$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alkyl; or $R^8$ in combination with $R^9$ forms a saturated 5- or 6-membered heterocycle that is a piperidine, a morpholine, a pyrrolidine or a piperazine, each of which is optionally substituted by methyl, carboxylic acid, a salt of carboxylic acid, or a carboxylic acid ester of a $C_1$–$C_6$ alkyl; or —L-$R_x$; or —L-$S_c$;

or $R^8$ in combination with $R^2$, or $R^9$ in combination with $R^3$, or both, form a 5- or 6-membered ring that is saturated or unsaturated, and is optionally substituted by one or more $C_1$–$C_6$ alkyls or —$CH_2SO_3X$ moieties;

C is $OR^{17}$ or $NR^{18}R^{19}$;

where $R^{17}$ is H, or $C_1$–$C_{18}$ alkyl; or —L-$R_x$; or —L-$S_c$;

where $R^{18}$ and $R^{19}$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alkyl; or $R^{18}$ in combination with $R^{19}$ forms a saturated 5- or 6-membered heterocycle that is a piperidine, a morpholine, a pyrrolidine or a piperazine, each of which is optionally substituted by methyl, carboxylic acid, a salt of carboxylic acid, or a carboxylic acid ester of a $C_1$–$C_6$ alkyl; or —L-$R_x$; or —L-$S_c$;

or $R^{18}$ in combination with $R^4$, or $R^{19}$ in combination with $R^5$, or both, form a 5- or 6-membered ring that is saturated or unsaturated, and is optionally substituted by one or more $C_1$–$C_6$ alkyls or —$CH_2SO_3X$ moieties;

B is O or $N^+R^{18}R^{19}$;

$R^{10}$ is H, F, CN, a carboxylic acid, a salt of carboxylic acid, or a carboxylic acid ester of a $C_1$–$C_6$ alcohol; or $R^{10}$ is a saturated or unsaturated $C_1$–$C_{18}$ alkyl that is optionally substituted one or more times by F, Cl, Br, carboxylic acid, a salt of carboxylic acid, a carboxylic acid ester of a $C_1$–$C_6$ alcohol, —$SO_3X$, amino, alkylamino, or dialkylamino, the alkyl groups of which have 1–6 carbons; or —L-$R_x$; or —L-$S_c$; or $R^{10}$ has the formula

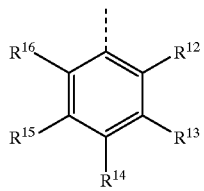

where $R^{12}$, $R^{13}$, $R^{14}$, $R^{15}$ and $R^{16}$ are independently H, F, Cl, Br, I, —$SO_3X$, a carboxylic acid, a salt of carboxylic acid, CN, nitro, hydroxy, azido, amino, hydrazino; or —L-$R_x$; or —L-$S_c$; or $C_1$–$C_{18}$ alkyl, $C_1$–$C_{18}$ alkoxy, $C_1$–$C_{18}$ alkylthio, $C_1$–$C_{18}$ alkanoylamino, $C_1$–$C_{18}$ alkylaminocarbonyl, $C_2$–$C_{36}$ dialkylaminocarbonyl, $C_1$–$C_{18}$ alkyloxycarbonyl, or $C_6$–$C_{18}$ arylcarboxamido, the alkyl or aryl portions of which are optionally substituted one or more times by F, Cl, Br, I, hydroxy, carboxylic acid, a salt of carboxylic acid, a carboxylic acid ester of a $C_1$–$C_6$ alcohol, —$SO_3X$, amino, alkylamino, dialkylamino or alkoxy, the alkyl portions of each having 1–6 carbons; or one pair of adjacent substituents $R^{13}$ and $R^{14}$, $R^{14}$ and $R^{15}$ or $R^{15}$ and $R^{16}$, when taken in combination, form a fused 6-membered aromatic ring that is optionally further substituted by carboxylic acid, or a salt of carboxylic acid; and $R^{11}$ is H, hydroxy, CN or a $C_1$–$C_6$ alkoxy; or $R^{10}$ in combination with $R^{11}$ forms a 5-membered spirolactone ring or a 5-membered spirosultone ring; or $R^{11}$ in combination with $R^{12}$ forms a 5- or 6-membered spirolactone ring or a 5- or 6-membered spirosultone ring that is optionally and independently substituted by H, F or $CH_3$; or $R^{10}$ when taken in combination with $R^{11}$ is a carbonyl oxygen;

each L is a covalent linkage; each $R_x$ is a reactive group; and each $S_c$ is a conjugated substance;

provided that either at least one of $R^2$, $R^3$, $R^4$, and $R^5$ is —$SO_3X$; or $R^8$ in combination with $R^2$, $R^9$ in combination with $R^3$, or $R^{18}$ in combination with $R^4$, or $R^{19}$ in combination with $R^5$, form a 5- or 6-membered ring that is saturated or unsaturated, and is substituted at a carbon atom by at least one —$CH_2SO_3X$ moiety;

with a biological sample in a concentration sufficient to yield a detectable optical response under the desired conditions.

54. A method, as claimed in claim 53, further comprising combining the sample with an additional detection reagent that has spectral properties that are detectably different from said optical response.

55. A method, as claimed in claim 53, further comprising the step of determining a characteristic of the sample by comparing the optical response with a standard response parameter.

56. A method, as claimed in claim 55, wherein the sample comprises cells, and the characteristic determined is the viability of the cells.

57. A method, as claimed in claim 53, wherein the sample comprises cells, and the step of combining comprises electroporation, shock treatment, high extracellular ATP, pressure microinjection, scrape loading, patch clamp loading, or phagocytosis.

58. A method, as claimed in claim 53, further comprising tracing the temporal or spatial location of the optical response within the sample.

59. A method, as claimed in claim 53, wherein each L is independently a single covalent bond, or L is a covalent linkage having 1–24 nonhydrogen atoms selected from the group consisting of C, N, O, P, and S and is composed of any combination of single, double, triple or aromatic carbon-carbon bonds, carbon-nitrogen bonds, nitrogen-nitrogen bonds, carbon-oxygen bonds, carbon-sulfur bonds, phosphorus-oxygen bonds, and phosphorus-nitrogen bonds.

60. A method, as claimed in claim 53, wherein for said compound at least one of $R^{13}$, $R^{14}$, $R^{15}$ and $R^{16}$ is —L-$R_x$ or —L-$S_c$;

$R_x$ is a carboxylic acid, an activated ester of a carboxylic acid, an amine, an azide, a hydrazine, a haloacetamide, an alkyl halide, an isothiocyanate, or a maleimide group; and $S_c$ is a peptide, a protein, a polysaccharide, a nucleic acid polymer, an ion-complexing moiety, a lipid, or a non-biological organic polymer or polymeric microparticle, that is optionally bound to one or more additional fluorophores that are the same or different.

61. A method, as claimed in claim 53, wherein for said compound at least one of $R^{13}$, $R^{14}$, $R^{15}$, and $R^{16}$ is —L-$S_c$;

and $S_c$ is an antibody to a fluorophore.

62. A method, as claimed in claim 53, wherein for said compound A is $NR^8R^9$, B is $N^+R^{18}R^{19}$, and C is $NR^{18}R^{19}$.

63. A method, as claimed in claim 62, wherein said compound has the formula

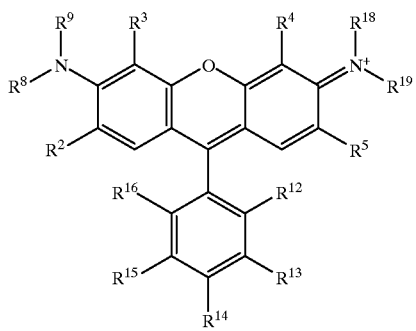

wherein $R^2$, $R^3$, $R^4$ and $R^5$ are independently H, F, Cl, Br, I, $C_1$–$C_{18}$ alkyl, $C_1$–$C_{18}$ alkoxy, or —$SO_3X$;

$R^8$ and $R^9$ are independently H, $C_1$–$C_6$ alkyl, $C_1$–$C_6$ carboxyalkyl, a salt of $C_1$–$C_6$ carboxyalkyl, $C_1$–$C_6$ sulfoalkyl, or a salt of $C_1$–$C_6$ sulfoalkyl; or $R^8$ in combination with $R^2$ forms a 5- or 6-membered ring that is saturated or unsaturated, and that is optionally substituted by one or more $C_1$–$C_6$ alkyls or —$CH_2SO_3X$ moieties;

$R^{18}$ and $R^{19}$ are independently H, $C_1$–$C_6$ alkyl, $C_1$–$C_6$ carboxyalkyl, a salt of $C_1$–$C_6$ carboxyalkyl, $C_1$–$C_6$ sulfoalkyl, or a salt of $C_1$–$C_6$ sulfoalkyl; or $R^{19}$ in combination with $R^5$ forms a 5- or 6-membered ring that is saturated or unsaturated, and that is optionally substituted by one or more $C_1$–$C_6$ alkyls or —$CH_2SO_3X$ moieties;

$R^{12}$, $R^{13}$, $R^{14}$, $R^{15}$ and $R^{16}$ are independently H, Cl, F, amino, nitro, —$SO_3X$, a carboxylic acid, a salt of carboxylic acid, or —S-$(CH_2)_n$COOH where n=1–15;

provided that $R^3$ and $R^4$ are each —$SO_3X$;

or $R^8$ in combination with $R^2$ forms a 5- or 6-membered ring that is saturated or unsaturated, and is substituted by —$CH_2SO_3X$; and $R^{19}$ in combination with $R^5$ forms a 5- or 6-membered ring that is saturated or unsaturated, and is substituted at a carbon atom by —$CH_2SO_3X$.

64. A method, as claimed in claim 53, wherein for said compound at least one of $R^{13}$, $R^{14}$, $R^{15}$, and $R^{16}$ is —L-$S_c$;

and $S_c$ is an antibody to an antibody that is present in said sample.

65. A compound having the formula

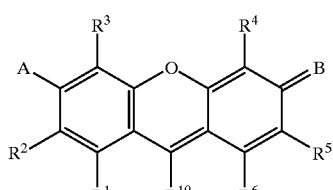

or the formula

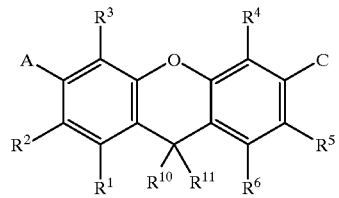

wherein $R^2$, $R^3$, $R^4$ and $R^5$ are independently H, F, Cl, Br, I, CN; or $C_1$–$C_{18}$ alkyl, or $C_1$–$C_{18}$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol; or —L-$R_x$; or —$SO_3X$ where X is H or a counterion $R^1$ and $R^6$ are H; or $R^1$ taken in combination with $R^2$, or $R^5$ taken in combination with $R^6$, or both, form a fused aromatic six membered ring that is optionally substituted one or more times by —$SO_3X$;

A is $OR^7$, $R^7$ is H, $C_1$–$C_{18}$ alkyl; or —L-$R_x$;

C is $OR^{17}$;

where $R^{17}$ is H, or $C_1$–$C_{18}$ alkyl; or —L-$R_x$;

B is O;

$R^{10}$ has the formula

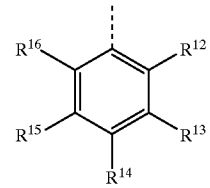

where $R^{12}$, $R^{13}$, $R^{14}$, $R^{15}$ and $R^{16}$ are independently H, F, Cl, Br, I, —$SO_3X$, a carboxylic acid, a salt of carboxylic acid, CN, nitro, hydroxy, azido, amino, hydrazino; or —L-$R_x$; or $C_1$–$C_{18}$ alkyl, $C_1$–$C_{18}$ alkoxy, $C_1$–$C_{18}$ alkylthio, $C_1$–$C_{18}$ is alkanoylamino, $C_1$–$C_{18}$ alkylaminocarbonyl, $C_2$–$C_{36}$ dialkylaminocarbonyl, $C_1$–$C_{18}$ alkyloxycarbonyl, or $C_6$–$C_{18}$ arylcarboxamido, the alkyl or aryl portions of which are optionally substituted one or more times by F, Cl, Br, I, hydroxy, carboxylic acid, a salt of carboxylic acid, a carboxylic acid ester of a $C_1$–$C_6$ alcohol, —$SO_3X$, amino, alkylamino, dialkylamino or alkoxy, the alkyl portions of each having 1–6 carbons; or one pair of adjacent substituents $R^{13}$ and $R^{14}$, $R^{14}$ and $R^{15}$ or $R^{15}$ and $R^6$, when taken in combination, form a fused 6-membered aromatic ring that is optionally further substituted by carboxylic acid, or a salt of carboxylic acid; and $R^{11}$ is H, hydroxy, CN or a $C_1$–$C_6$ alkoxy; or $R^{10}$ in combination with $R^{11}$ forms a 5-membered spirolactone ring or a 5-membered spirosultone ring; or $R^{11}$ in combination with $R^{12}$ forms a 5- or 6-membered spirolactone ring or a 5- or 6-membered spirosultone ring that is optionally and independently substituted by H, F or $CH_3$; or $R^{10}$ when taken in combination with $R^{11}$ is a carbonyl oxygen;

for all —L-$R_x$, each L is a covalent linkage; and $R_x$ is a reactive group;

provided that at least two of $R^2$, $R^3$, $R^4$, and $R^5$ is —$SO_3X$; and that at least one of $R^2$, $R^3$, $R^4$, $R^5$, $R^7$, $R^8$, $R^9$, $R^{10}$, $R^{12}$, $R^{13}$, $R^{14}$, $R^{15}$, $R^{16}$, $R^{17}$ is —L-$R_x$.

66. A compound, as claimed in claim 65, wherein one of $R^{13}$, $R^{14}$, $R^{15}$, and $R^{16}$ is —L-$R_x$.

67. A compound, as claimed in claim 65, wherein $R^3$ and $R^4$ are each —$SO_3X$.

68. A compound, as claimed in claim 65, wherein $R^{12}$ is a carboxylic acid, a salt of carboxylic acid, or —$SO_3X$; and $R^{11}$ is not present.

69. A compound, as claimed in claim 65, wherein each L is independently a single covalent bond, or L is a covalent linkage having 1–24 nonhydrogen atoms selected from the group consisting of C, N, O, P, and S and is composed of any combination of single, double, triple or aromatic carbon-carbon bonds, carbon-nitrogen bonds, nitrogen-nitrogen bonds, carbon-oxygen bonds, carbon-sulfur bonds, phosphorus-oxygen bonds, and phosphorus-nitrogen bonds.

70. A compound, as claimed in claim 65, wherein $R_x$ is an acrylamide, an activated ester of a carboxylic acid, hydroxy, an aldehyde, an alkyl halide, a sulfonate, an amine, an anhydride, an aniline, an aryl halide, an azide, an aziridine, a boronate, a carboxylic acid, a carbodiimide, a diazoalkane, an epoxide, a glycol, a haloacetamide, a halotriazine, a hydrazine, a hydroxylamine, an imido ester, an isocyanate, an isothiocyanate, a ketone, a maleimide, a phosphoramidite, a sulfonyl halide, or a thiol group.

71. A compound, as claimed in claim 65, wherein L is a single covalent bond and $R_x$ is a carboxylic acid, an activated ester of a carboxylic acid, an amine, an azide, a hydrazine, a haloacetamide, an alkyl halide, an isothiocyanate, or a maleimide group.

72. A compound, as claimed in claim 33, wherein the conjugated substance is a nucleic acid base, nucleoside, nucleotide, or a nucleic acid polymer.

73. A compound, as claimed in claim 72, wherein the conjugated substance is a nucleoside triphosphate, a deoxynucleoside triphosphate, or a dideoxynucleoside triphosphate.

* * * * *

UNITED STATES PATENT AND TRADEMARK OFFICE
CERTIFICATE OF CORRECTION

PATENT NO. : 6,130,101  Page 1 of 1
DATED : October 10, 2000
INVENTOR(S) : Mao et al.

It is certified that error appears in the above-identified patent and that said Letters Patent is hereby corrected as shown below:

Column 32,
Lines 19-20, "21.1 mol" should read -- 21.1µmol --.

Column 51,
Line 11, "R9" should read -- R8 --.

Column 53,
Line 64, "C1-C8" should read -- C1-C18 --.

Column 58,
Line 51, "R6" should read -- R16 --.

Signed and Sealed this

Seventeenth Day of September, 2002

Attest:

JAMES E. ROGAN
Attesting Officer  Director of the United States Patent and Trademark Office